United States Patent
Imgrund et al.

(10) Patent No.: US 8,118,593 B2
(45) Date of Patent: *Feb. 21, 2012

(54) METHOD AND SYSTEM FOR ENHANCED ORTHODONTIC TREATMENT PLANNING

(75) Inventors: Hans Imgrund, Berlin (DE); Peer Sporbert, Berlin (DE); Claudia Strauss, Berlin (DE)

(73) Assignee: Orametrix, Inc., Richardson, TX (US)

( * ) Notice: Subject to any disclaimer, the term of this patent is extended or adjusted under 35 U.S.C. 154(b) by 8 days.

This patent is subject to a terminal disclaimer.

(21) Appl. No.: 12/776,328

(22) Filed: May 7, 2010

(65) Prior Publication Data

US 2010/0223034 A1 Sep. 2, 2010

Related U.S. Application Data

(60) Division of application No. 12/106,985, filed on Apr. 21, 2008, now Pat. No. 7,744,369, which is a continuation of application No. 11/525,453, filed on Sep. 23, 2006, now Pat. No. 7,361,018, which is a continuation-in-part of application No. 10/620,231, filed on Jul. 14, 2003, now Pat. No. 7,156,655, which is a continuation-in-part of application No. 10/428,461, filed on May 2, 2003, now Pat. No. 7,717,708, said application No. 11/525,453 is a continuation-in-part of application No. 11/233,623, filed on Sep. 23, 2005, now Pat. No. 7,695,278, which is a continuation-in-part of application No. 11/133,996, filed on May 20, 2005, now Pat. No. 8,021,147.

(51) Int. Cl.
*A61C 3/00* (2006.01)

(52) U.S. Cl. ........................................ 433/24

(58) Field of Classification Search ............... 433/24, 433/213, 214, 229; 700/98
See application file for complete search history.

(56) References Cited

U.S. PATENT DOCUMENTS

| | | | |
|---|---|---|---|
| 6,250,918 B1 * | 6/2001 | Sachdeva et al. | 433/24 |
| 6,632,089 B2 * | 10/2003 | Rubbert et al. | 433/24 |
| 2006/0147872 A1 * | 7/2006 | Andreiko | 433/24 |

* cited by examiner

*Primary Examiner* — Sunil K Singh
(74) *Attorney, Agent, or Firm* — Jasvantrai C. Shah

(57) ABSTRACT

A method and system are disclosed for quickly arriving at a pre-set-up for the orthodontic treatment of a patient based up on the user specified parameters; and thereafter enabling the user in interactively arriving at a final, desired treatment set-up for the patient. Several sub-operations are disclosed for arriving at the orthodontic pre-set-up. These sub-operations can be arranged in a specific sequence for realizing the orthodontic treatment pre-set-up for a patient. According to another aspect of the invention, a global reference system is disclosed that enables consistent treatment planning. The global reference system prevents unintended tooth displacements caused as side effects to the desired tooth displacements.

9 Claims, 22 Drawing Sheets

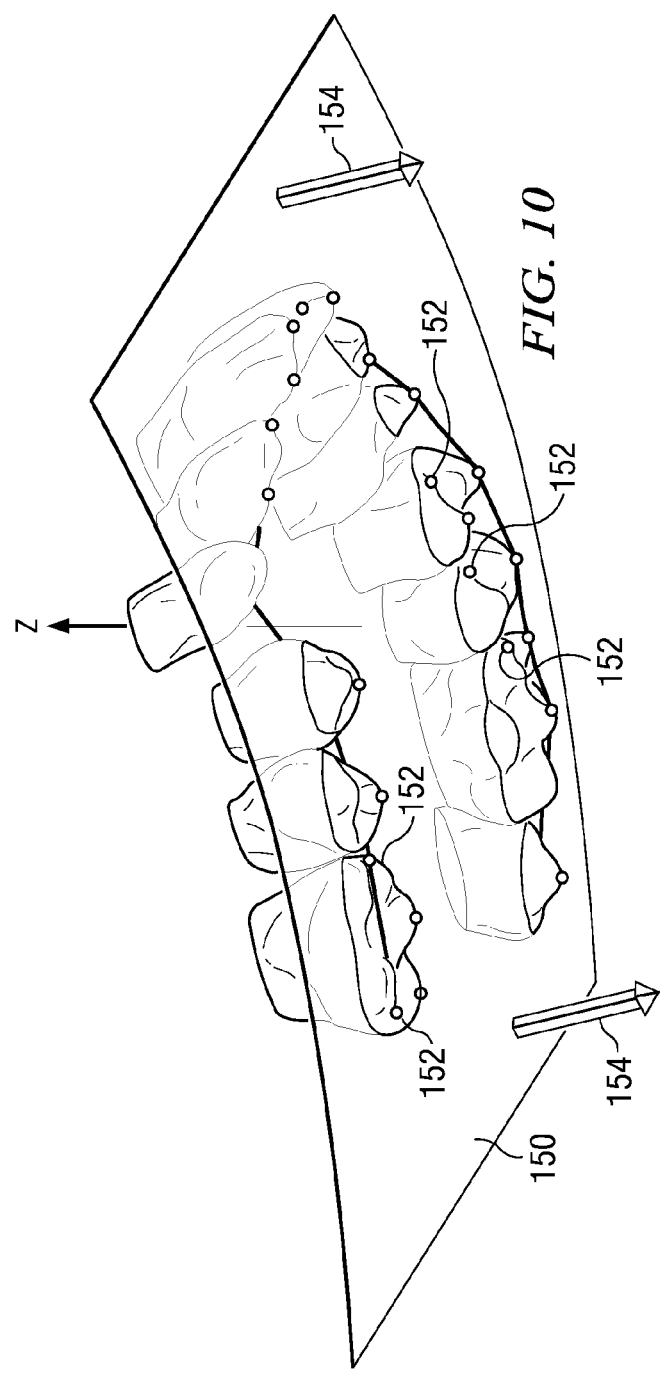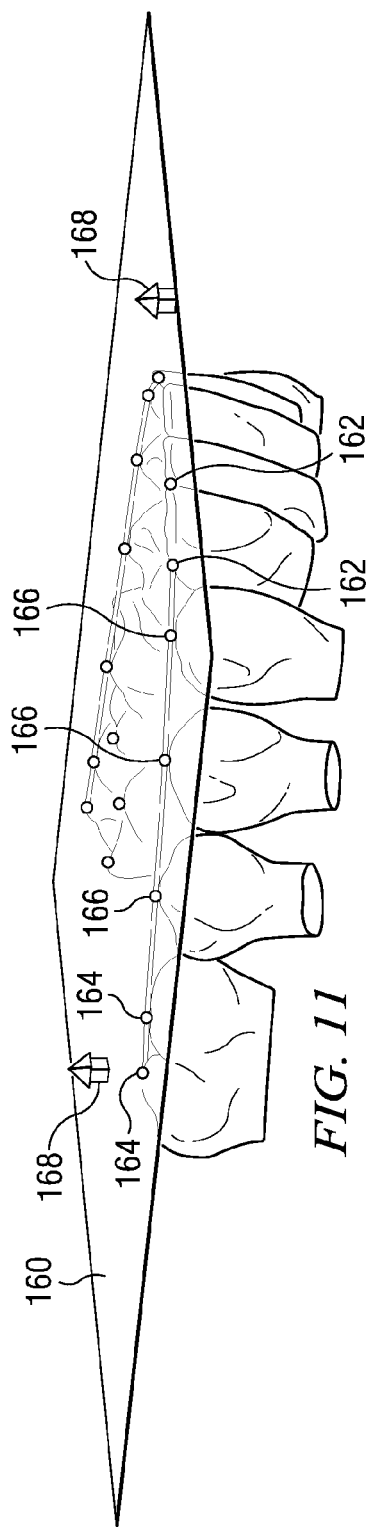

METHOD AND SYSTEM FOR ENHANCED ORTHODONTIC TREATMENT PLANNING

CROSS-REFERENCE TO RELATED APPLICATIONS

This is a divisional application of the application Ser. No. 12/106,985, filed Apr. 21, 2008, now issued as U.S. Pat. No. 7,744,369, which is a continuation application of Ser. No. 11/525,453, filed Sep. 23, 2006, now issued as U.S. Pat. No. 7,361,018, which is a continuation-in-part of application Ser. No. 10/620,231 filed Jul. 14, 2003, now issued as U.S. Pat. No. 7,156,655, which is a continuation-in-part of application Ser. No. 10/428,461 filed May 2, 2003, now U.S. Pat. No. 7,717,708; and a continuation-in-part of application Ser. No. 11/233,623 filed Sep. 23, 2005, now issued as U.S. Pat. No. 7,695,278, which is a continuation-in-part of application Ser. No. 11/133,996, filed May 20, 2005, now U.S. Pat. No. 8,021,147; and related to application Ser. No. 11/234,591, filed Sep. 23, 2005, pending. The entire contents of each of the above listed applications are incorporated by reference herein.

BACKGROUND OF THE INVENTION

A. Field of the Invention

This invention relates to the field of computerized techniques for orthodontic treatment planning for human patients. More particularly, the invention is directed to providing a method and system for quickly arriving at a pre-set-up for the orthodontic treatment of a patient based up on the user specified parameters; and thereafter enabling the user in interactively arriving at a final, desired treatment set-up for the patient.

B. Description of Related Art

The traditional process of diagnosis and treatment planning for a patient with orthodontic problems or disease typically consists of the practitioner obtaining clinical history, medical history, dental history, and orthodontic history of the patient supplemented by 2D photographs, 2D radiographic images, CT scans, 2D and 3D scanned images, ultrasonic scanned images, and in general non-invasive and sometimes invasive images, plus video, audio, and a variety of communication records. Additionally, physical models, such as made from plaster of paris, of the patient's teeth are created from the impressions taken of the patient's upper and lower jaws. Often, such models are manually converted into teeth drawings by projecting teeth on drawing paper. Thus, there is a large volume of images and data involved in the diagnosis and treatment planning process. Furthermore, the information may require conversion from one form to another and selective reduction before it could become useful. There are some computerized tools available to aid the practitioner in these data conversion and reduction steps, for example to convert cephalometric x-rays (i.e., 2 dimensional x-ray photographs showing a lateral view of the head and jaws, including teeth) into points of interest with respect to soft tissue, hard tissue, etc., but they are limited in their functionalities and scope. Even then, there is a fairly substantial amount of manual work involved in these steps.

Consequently, the practitioner is left to mental visualization, chance process to select the treatment course that would supposedly work. Furthermore, the diagnosis process is some-what ad-hoc and the effectiveness of the treatment depends heavily upon the practitioner's level of experience. Often, due to the complexities of the detailed steps and the time consuming nature of them, some practitioners take a shortcut, relying predominantly on their intuition to select a treatment plan. For example, the diagnosis and treatment planning is often done by the practitioner on a sheet of acetate placed over the X-rays. All of these factors frequently contribute towards trial and error, hit-and-miss, lengthy and inefficient treatment plans that require numerous mid-course adjustments. While at the beginning of treatment things generally run well as all teeth start to move at least into the right direction, at the end of treatment a lot of time is lost by adaptations and corrections required due to the fact that the end result has not been properly planned at any point of time. By and large, this approach lacks reliability, reproducibility and precision. More over, there is no comprehensive way available to a practitioner to stage and simulate the treatment process in advance of the actual implementation to avoid the often hidden pitfalls. And the patient has no choice and does not know that treatment time could be significantly reduced if proper planning was done.

In recent years, computer-based approaches have been proposed for aiding orthodontists in their practice. See Andreiko, U.S. Pat. No. 6,015,289; Snow, U.S. Pat. No. 6,068,482; Kopelmann et al., U.S. Pat. No. 6,099,314; Doyle, et al., U.S. Pat. No. 5,879,158; Wu et al., U.S. Pat. No. 5,338,198, and Chisti et al., U.S. Pat. Nos. 5,975,893 and 6,227,850, the contents of each of which is incorporated by reference herein. Also see imaging and diagnostic software and other related products marketed by Dolphin Imaging, 6641 Independence Avenue, Canoga Park, Calif. 91303-2944.

U.S. Pat. No. 6,648,640 to Rubbert, et al. describes an interactive, computer based orthodontist treatment planning, appliance design and appliance manufacturing. A scanner is described which acquires images of the dentition, which are converted to three-dimensional frames of data. The data from the several frames are registered to each other to provide a complete three-dimensional virtual model of the dentition. Individual tooth objects are obtained from the virtual model. A computer-interactive software program provides for treatment planning, diagnosis and appliance design from the virtual tooth models. A desired occlusion for the patient is obtained from the treatment planning software. The virtual model of the desired occlusion and the virtual model of the original dentition provide a base of information for custom manufacture of an orthodontic appliance. A variety of possible appliance and appliance manufacturing systems are contemplated, including customized arch wires and customized devices for placement of off-the shelf brackets on the patient's dentition for housing the arch wires, and removable orthodontic appliances.

U.S. Pat. No. 6,632,089 to Rubbert, et al. describes an interactive, software-based treatment planning method to correct a malocclusion. The method can be performed on an orthodontic workstation in a clinic or at a remote location such as a lab or precision appliance-manufacturing center. The workstation stores a virtual three-dimensional model of the dentition of a patient and patient records. The virtual model is manipulated by the user to define a target situation for the patient, including a target arch-form and individual tooth positions in the arch-form. Parameters for an orthodontic appliance, such as the location of orthodontic brackets and resulting shape of an orthodontic arch wire, are obtained from the simulation of tooth movement to the target situation and the placement position of virtual brackets. The treatment planning can also be executed remotely by a precision appliance service center having access to the virtual model of the dentition. In the latter situation, the proposed treatment plan is sent to the clinic for review, and modification or approval by the orthodontist. The method is suitable for other orthodontic appliance systems, including removable appliances such as transparent aligning trays.

Other background references related to capturing three dimensional models of dentition and associated craniofacial structures include S. M. Yamany and A. A. Farag, "A System for Human Jaw Modeling Using Intra-Oral Images" in *Proc. IEEE Eng. Med. Biol. Soc. (EMBS) Conf.*, Vol. 20, Hong Kong, October 1998, pp. 563-566; and M. Yamany, A. A. Farag, David Tasman, A. G. Farman, "A 3-D Reconstruction System for the Human Jaw Using a Sequence of Optical Images," *IEEE Transactions on Medical Imaging*, Vol. 19, No. 5, May 2000, pp. 538-547. The contents of these references are incorporated by reference herein.

The technical literature further includes a body of literature describing the creation of 3D models of faces from photographs, and computerized facial animation and morphable modeling of faces. See, e.g., Pighin et al., *Synthesizing Realistic Facial Expression from Photographs*, Computer Graphics Proceedings SIGGRAPH '98, pp. 78-94 (1998); Pighin et al., *Realistic Facial Animation Using Image-based 3D Morphing*, Technical Report no. UW-CSE-97-01-03, University of Washington (May 9, 1997); and Blantz et al., *A Morphable Model for The Synthesis of 3D Faces*, Computer Graphics Proceedings SIGGRAPH '99 (August, 1999). The contents of these references are incorporated by reference herein.

U.S. Pat. No. 6,616,444 to Andreiko, et al. describes a system and method by which an orthodontic appliance is automatically designed and manufactured from digital lower jaw and tooth shape data of a patient. The method provides for scanning a model of the patient's mouth to produce two or three dimensional images and digitizing contours and selected points. A computer may be programmed to construct archforms and/or to calculate finish positions of the teeth, then to design an appliance to move the teeth to the calculated positions.

U.S. Pat. No. 6,322,359 to Jordan, et al. describes a computer implemented method of creating a dental model for use in dental articulation. The method provides a first set of digital data corresponding to an upper arch image of at least a portion of an upper dental arch of a patient, a second set of digital data corresponding to a lower arch image of at least a portion of a lower dental arch of the patient, and hinge axis data representative of the spatial orientation of at least one of the upper and lower dental arches relative to a condylar axis of the patient. A reference hinge axis is created relative to the upper and lower arch images based on the hinge axis data. Further, the method may include bite alignment data for use in aligning the lower and upper arch images. Yet further, the method may include providing data associated with condyle geometry of the patient, so as to provide limitations on the movement of at least the lower arch image when the arch images are displayed. Further, a wobbling technique may be used to determine an occlusal position of the lower and upper dental arches. Various computer implemented methods of dental articulation are also described. For example, such dental articulation methods may include moving at least one of the upper and lower arch images to simulate relative movement of one of the upper and lower dental arches of the patient, may include displaying another image with the upper and lower dental arches of the dental articulation model, and/or may include playing back recorded motion of a patient's mandible using the dental articulation model.

The prior art computerized interactive treatment planning methods are relatively slow since they require the user to arrive at a desired treatment plan by manipulating the dentition of a patient typically one parameter at a time. Practitioners would greatly benefit from a digital orthodontic treatment planning process that is enhanced in terms of efficiency and quality. There definitely is room to improve the efficiency and quality of virtual orthodontic treatment planning. The invention disclosed herein offers a novel and enhanced method and system for digitally planning the orthodontic treatment with improved efficiency and quality.

SUMMARY OF THE INVENTION

In the first aspect of the invention, a method is provided for quickly arriving at a virtual pre-set-up of the orthodontic treatment plan for a patient, based up on the user specified parameters; and thereafter enabling the user interactively arrive at a final, desired treatment set-up for the patient. The parameter types and values utilized in the treatment planning process are common to the orthodontic discipline. Moreover, in one aspect of the invention, a default parameter set is provided that the user can optionally choose for obtaining the pre-set-up automatically. The method of creating the pre-set-up relies heavily on a set of parameters describing the jaw characteristics as well as the jaw interrelations. The tooth-root movements are confined to a necessary minimum as the pre-set-up meets various criteria towards an optimum. The pre-set-up method performs automatically all global tasks such as guidance of the tooth roots, adjustment of the intercuspidation of the molars, space management in the frontal area and creation of an occlusion to an optimum. The underlying mathematical model and rules consider typical details like frontal overjet, overbite and molar classes. It supports the space management for virtual or real tooth extractions. Space can also be reserved for later implantations. The method allows selection of global arch form to account for specific characteristics of a single jaw. Arch forms from the database library may be used (e.g. straight wire technique). Additionally, a method is provided for the user to derive the arch form manually, e.g., from the malocclusion. The method also enables the user in devising an oral surgery, when applicable and desired, such as maxillary or mandibular prognathism/retrognathism. The treatment planning process is divided into sub-operations that simulate the work-flow of an orthodontist or dental technician. The occlusion is formed independently from the global form of the jaw and vice versa; or the consequences from parameter changes like the AP position of the anterior teeth are be displayed instantaneously without modifying other constraints, such as the frontal overjet. The method can be summarized as follows:

1. obtain (a) a three-dimensional virtual model of a patient in malocclusion or any mid-treatment stage, and (b) tooth-features; and deriving there from;
2. derive (a) a global reference system, (b) Curve of Wilson (optional), molar torque, and (c) relations of upper and lower jaw;
3. sub-operations to generate the orthodontic pre-set-up
   (a) find the Alveolar Reference Curve;
   (b) determine the filter of controlled tipping of tooth-root including to parameterization of the controlled tipping filter;
   (c) find the occlusal surface;
   (d) vertically align the occlusal surface; (i) parameterize the occlusal surface; and (ii) parameterize the alignment operation on the occlusal surface;
   (e) find the arch form;
   (f) align teeth on the arch form spline;
   (f) parameterize the shape of the arch form spline: (i) derive of the arch form splines from a reference jaw; and (ii) derive the breadth of the jaw; and (g) parameterize the aligning on arch form: (i) AP-Position of the molars; (ii) interproximal distances; (iii) standardization of the frontal overjet; (iv) standardization of the molar relation (Angels classes); and (v) midline for the jaw specifically correction of the global facial midline.

The following is one possible automatic sequence of the usage of the sub-operations listed above, according to a preferred embodiment of the invention:

1. Activate the controlled tipping filter for all of the following operations;
2. Creation of the occlusal surface of the upper and lower jaw by using the indicated reference teeth of the malocclusion or of any other reference stage.
3. Creation of the arch form spline for the reference jaw by using the indicated reference teeth under consideration of the offset value of the AP-position of the front as well as of the desired symmetrical characteristic.
4. Determination of the relative transversal position of the incisal contact points by using the standardized offset value (midline)
5. Aligning on arch form spline. (horizontal correction of the position of the teeth) usage of eventually standardized fixed interproximal distances.
6. Aligning on the Occlusal Surface under consideration of potential offset values for the vertical position of the teeth.
7. A new aligning on arch form spline in order to correct interferences with the vertical alignment.
8. mesiodistal shift of the lateral segments in order to keep the sagittal position of the first molars e.g. under consideration of a possibly standardized offset value.
9. Adjustment of possibly created interproximal gaps or intersections in the front by the equal distribution of all created gaps or intersections on the individual interproximal space between the teeth on the left and the right half of the jaw.

Optional:

10. Automatic reduction of the interproximal gaps in the front by changing the AP-position of the front under consideration of possibly standardized maximum interproximal reduction values.

The following sequence of sub-operation is also a possible realization of the process, according to another preferred embodiment of the invention:

1. Activate the controlled tipping filter for all of the following operations.
2. Creation of the occlusal surface of the upper or lower jaw by using the indicated reference teeth of the malocclusion or of any other reference stage.
3. Creation of the arch form spline for the dependent jaw under consideration of the width of the reference jaw and of the AP-position of the front according to the desired frontal overjet. The symmetrical characteristic of the dependent jaw corresponds to that of the reference jaw.
4. Determination of the relative transversal position of the incisal contact points using the standardized offset value.
5. Aligning on arch form spline (horizontal correction of the positions of the teeth) Usage of possibly standardized fixed interproximal distances.
6. Aligning on the occlusal surface under consideration of possible offset values for the vertical position of the teeth (vertical correction of the positions of the teeth)
7. A new aligning on arch form spline in order to correct interferences with the vertical alignment.
8. Mesiodistal shift of the lateral segments for the standardization of the desired molar class.
9. Adjustment of possibly created interproximal gaps or intersections in the front by the equal distribution of all created gaps or intersections on the individual interproximal distances on the left and the right half of the jaw.

Unlike to the process for the creation of the reference jaw, here the part operation 10 is not available. This is because the observance of the frontal overjet demanded for the dependent jaw and the parallel expansion or reduction of the frontal area exclude each other.

In the connection of the process realised here, the automatic process for the dependent jaw will be accomplished again after the modification of the frontal area. Like this it is guaranteed that the frontal overjet corresponds to the standardized value at any time.

Alternative Possibilities for the Configuration of the Process

Besides the processes for the automatic creation of an orthodontic pre-set-up presented above, other sequences of the part operations are imaginable.

For example, an operation can be used for the approximation of a curve of Wilson. Or the order of the partial operations can be changed if necessary.

It is also imaginable, to e.g. extend the automatic space management in the frontal area, so that the positions of the canines are also corrected. Like this, gaps or intersection between the front teeth could be avoided through the usage of the created expansion or reduction of the jaw additionally. As a result e.g. the dependent jaw could be included in an automatic process of the space management, since further possibilities for the configuration of the offset would be created.

Principally all further correction can be included by iterative usage of the automatic process. By this iteration the reciprocal influence of the positions of the teeth, as they correspond to the partial operations, would be annulled.

For example, the aligning on occlusal surface for a tooth which has been moved horizontally is no longer correct with a curve of spee at hand. Continuous usage of the aligning on occlusal surface operation would correct such an error without modifying the positions of the teeth, which have not been moved.

It depends on the desired exactness, with which the intended positions of the teeth or the global quantity shall be achieved, whether such a possible iteration or the continuous usage of the part operations will be used. On the other hand there is of course the accomplishment of the usage. The compromise which is optimal for the user can be fulfilled in any case.

Occasionally there will be the demand only to treat one jaw, whereas the other one should not be corrected. This doesn't constitute a problem to the deduction of the jaw to be treated from the other one, because the Ok/UK relations rely on tooth features. Consequently the processes for the single jaws can also be used independently from each other. Of course the virtual teeth of the jaw not to be treated and their tooth features have to be at hand.

Another possibility for the configuration of the whole process is created, when the role of the reference jaw and the dependent jaw are swapped after one or several iteration steps. By this e.g. the part operation 10 of the reference jaw process for the space management in the front can be used for the previous dependent jaw. The previous reference jaw then becomes the dependent jaw, whose pre-set-up is now accommodated to the new frontal shape of the reference jaw.

The fundamental concept of using a jaw as reference jaw in order to deduct the dependent jaw from it, referring to specified figures, which is demonstrated here, is not imperative. By using the process for reference jaws for both jaws, completely independent pre-set-ups of the maxilla and the mandible are created.

According to another aspect of the invention, a global reference system is disclosed that enables consistent treatment planning. The global reference system prevents unintended tooth displacements caused as side effects to the desired tooth displacements.

Yet in another aspect of the invention, a system, comprising a computing device, memory, and a set of software instructions is provided for quickly arriving at a virtual pre-set-up of the orthodontic treatment plan for a patient, based up on the user specified parameters; and thereafter enabling the user interactively arrive at a final, desired treatment set-up for the patient. The parameter types and values utilized in the treatment planning process are common to the orthodontic discipline. Moreover, in one aspect of the invention, a default parameter set is provided that the user can optionally choose for obtaining the pre-set-up automatically. The software instructions provided for creating the pre-set-up relies heavily on a set of parameters describing the jaw characteristics as well as the jaw interrelations. The tooth-root movements are confined to a necessary minimum as the pre-set-up meets various criteria towards an optimum. The pre-set-up software instructions perform automatically all global tasks such as guidance of the tooth roots, adjustment of the intercuspidation of the molars, space management in the frontal area and creation of an occlusion to an optimum. The underlying mathematical model and rules consider typical details like frontal overjet, overbite and molar classes. It supports the space management for virtual or real tooth extractions. Space can also be reserved for later implantations. The software instructions allow selection of global arch form to account for specific characteristics of a single jaw. Arch forms from the database library may be used (e.g. straight wire technique). Additionally, a method is provided for the user to derive the arch form manually, e.g., from the malocclusion. The method also enables the user in devising an oral surgery, when applicable and desired, such as maxillary or mandibular prognathism/retrognathism. The treatment planning process is divided into sub-operations that simulate the work-flow of an orthodontist or dental technician. The occlusion is formed independently from the global form of the jaw and vice versa; or the consequences from parameter changes like the AP position of the anterior teeth are be displayed instantaneously without modifying other constraints, such as the frontal overjet. The operations enabled by the software instructions can be summarized as follows:

1. obtain (a) a three-dimensional virtual model of a patient in malocclusion or any mid-treatment stage, and (b) tooth-features; and deriving there from;

2. derive (a) a global reference system, (b) Curve of Wilson (optional), molar torque, and (c) relations of upper and lower jaw;

3. sub-operations to generate the orthodontic pre-set-up
   (a) find the Alveolar Reference Curve;
   (b) determine the filter of controlled tipping of tooth-root including parameterization of the controlled tipping filter;
   (c) find the occlusal surface;
   (d) vertically align the occlusal surface; (i) parameterize the occlusal surface; and (ii) parameterize the alignment operation on the occlusal surface;
   (e) find the arch form;
   (f) align teeth on the arch form spline;
   (f) parameterize the shape of the arch form spline: (i) derive of the arch form splines from a reference jaw; and (ii) derive the breadth of the jaw; and
   (g) parameterize the aligning on arch form: (i) AP-Position of the molars; (ii) interproximal distances; (iii) standardization of the frontal overjet; (iv) standardization of the molar relation (Angels classes); and (v) midline for the jaw specifically correction of the global facial midline.

BRIEF DESCRIPTION OF THE DRAWINGS

Presently preferred embodiments of the invention are described below in reference to the appended drawings, wherein like reference numerals refer to like elements in the various views, and in which:

FIG. 10 shows an example of the occlusal surface for an upper jaw.

FIG. 11 shows the result of aligning the teeth to the occlusal surface of FIG. 9.

FIG. 33A shows the treatment pre-set-up from the labial view. FIG. 33B shows the same pre-set-up as in FIG. 33A from the left buccal point of view. FIG. 33C shows the same pre-set-up as in FIG. 33A from the right buccal point of view. FIG. 33D shows the same pre-set-up as in FIG. 33A from the lingual of view.

DETAILED DESCRIPTION OF PREFERRED EMBODIMENTS

Overview

Figure 1:
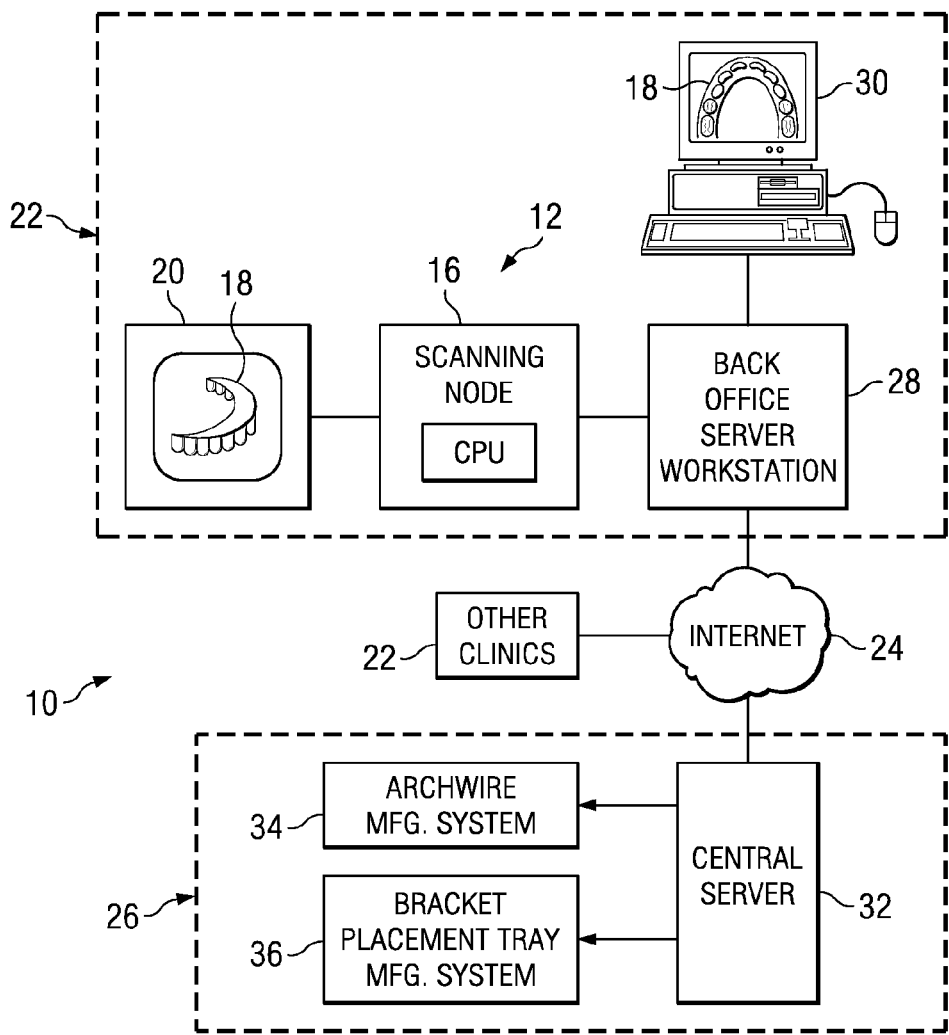
FIG. 1 is an illustration of an orthodontic care system incorporating a scanner system. The scanner is used by the orthodontist or the assistant to acquire three-dimensional information of the dentition and associated anatomical structures of a patient and provide a base of information to diagnose and plan treatment for the patient.

FIG. 1 is an illustration of an orthodontic care system 10 incorporating a scanner system 12. The scanner system is used to acquire three-dimensional information of the dentition and associated anatomical structures of a patient. The scanner system may comprise a CT scanner, a hand held scanner, a laser scanner or any other scanning device. The images could be acquired from a physical plaster model, an impression, or in-vivo scanning of the dentition and associated anatomical structures of a patient, or otherwise. The images are processed in a scanning node or workstation 16 having a central processing unit, such as a general-purpose computer. The scanning node 16, either alone or in combination with a back-office server 28, generates a three-dimensional computer model 18 of the dentition that provides the orthodontist with a base of information for diagnosis, planning treatment, and monitoring care for the patient. The model 18 is displayed to the user on a monitor 20 connected to the scanning node 16.

As noted above, the scanner system 12 is optimized for in-vivo scanning of teeth, or alternatively, scanning a plaster model of the teeth and/or an impression of the teeth.

The orthodontic care system consists of a plurality of orthodontic clinics 22 which are linked via the Internet or other suitable communications medium 24 (such as the public switched telephone network, cable network, etc.) to a precision appliance service center 26. Each clinic 22 has a back office server work station 28 having its own user interface, including a monitor 30. The back office server 28 executes an orthodontic treatment planning software program. The software obtains the three-dimensional digital data of the patient's teeth from the scanning node 16 and displays the model 18 for the orthodontist. The treatment planning software includes features to enable the orthodontist to manipulate the model 18 to plan treatment for the patient. The software moves the virtual teeth in accordance with the selections of the orthodontist. The software also allows the orthodontist to selectively place virtual brackets on the tooth models and design a customized archwire for the patient given the selected bracket positions. When the orthodontist has finished designing the orthodontic appliance for the patient, digital information regarding the patient, the malocclusion, and a desired treatment plan for the patient is sent over the communications medium to the appliance service center 26. A customized orthodontic archwire and a device for placement of the brackets on the teeth at the selected location is manufactured at the service center and shipped to the clinic 22.

As shown in FIG. 1, the precision appliance service center 26 includes a central server 32, an arch wire manufacturing system 34 and a bracket placement manufacturing system 36. For more details on these aspects of the illustrated orthodontic care system, the interested reader is directed to the patent application of Rüdger Rubbert et al., filed Apr. 13, 2001, entitled INTERACTIVE AND ARCHWIRE-BASED ORTHODONTIC CARE SYSTEM BASED ON INTRA-ORAL SCANNING OF TEETH, Ser. No. 09/835,039, now issued as U.S. Pat. No. 6,648,640, the entire contents of which are incorporated by reference herein.

The virtual model of the patient's dentition, and the individual tooth objects provide a base for diagnostic analysis of the dentition and treatment planning. Treatment planning software is provided on the workstation of the orthodontic clinic, and possibly at other remote locations such as the precision appliance center of FIG. 1. The treatment planning software can be considered an interactive, computer-based computer aided design and computer aided manufacturing (CAD/CAM) system for orthodontics. The apparatus is highly interactive, in that it provides the orthodontist with the opportunity to both observe and analyze the current stage of the patient's condition, and to develop and specify a target or desired stage. Further, the apparatus provides for simulation of tooth movement between current and target stages. For further details on treatment planning, refer to the previously mentioned patent application of Rüdger Rubbert et al., filed Apr. 13, 2001, entitled INTERACTIVE AND ARCHWIRE-BASED ORTHODONTIC CARE SYSTEM BASED ON INTRA-ORAL SCANNING OF TEETH, Ser. No. 09/835,039, now issued as U.S. Pat. No. 6,648,640, the entire contents of which are incorporated by reference herein.

The computerized treatment planning process can be greatly expedited and aided by employing applicable mathematical tools and rules based approach when realizing an orthodontic treatment set-up. However, the human anatomy is complex and varies from patient to patient, so one cannot solely rely upon mathematics and generic rules to automatically produce a desired final orthodontic treatment plan for a particular patient. Indeed, typically the final desired tooth positions could be obtained only partly from a mathematical model. The practitioner or the user with the necessary orthodontic background must be able to play a decisive role on the form of the final desired orthodontic treatment set-up. Therefore, there is a need to create tools employing mathematical models for orthodontic treatment planning wherein the user is given control to interactively influence the desired characteristics for a specific orthodontic case. One skilled in the art would appreciate that a parameterization of the mathematical model is desired using values and representations common to the orthodontic discipline. To this end, a default parameter set can be defined enabling a user realize the orthodontic treatment set-up expeditiously as a first step in the interactive treatment planning process.

So, the task of the mathematical models and rules is to create a set-up relying on a set of parameters describing the jaw characteristics as well as the jaw interrelations. The tooth root movements should be confined to a minimum and the treatment set-up should meet various criteria, such as those described in application Ser. No. 11/133,996, filed May 20, 2005, pending, so as to be the most desirable treatment set-up for the patient.

Furthermore, the enhanced treatment planning process disclosed herein performs automatically all global tasks like guidance of the tooth roots, adjustment of the intercuspidation of the molars, space management in the frontal area and creation of an occlusion to an optimum condition.

The enhanced treatment planning process disclosed herein also considers typical details like frontal overjet, overbite and molar classes. It also supports space management for virtual or real tooth extractions or carry it through automatically. It further enables a practitioner or a user to reserve the space for later implantations.

The global arch form type is selectable to account for specific characteristics of a single jaw. Also, the arch forms from the literature may be used (e.g. Straight Wire Technique), but arch forms derived naturally, e.g. from the malocclusion should be possible as well.

The treatment planning method permits an option to support oral surgery, such as maxillary or mandibular prognathism/retrognathism.

The automated treatment-planning algorithm is divided in sub-operations that simulate the work-flow of an orthodontist or dental technician so as to make it easier to enter relevant non-mathematical treatment data and procedures.

That means, the occlusion is formed independently from the global form of the jaw and vice versa; or consequences from parameter changes like the AP position of the anterior teeth should be displayed instantaneously without modifying other constraints, such as the frontal overjet.

The user may specify the parameters in a way such that it cannot lead to a consistent orthodontic set-up. The most probably arising contradiction out of this will lie in lack or abundance of space, as it is the case with manual set-ups realized on a plaster model. In such a case the system quantifies the resulting contradictions and helps the user to solve the problem quickly and adequately.

For the virtual orthodontic treatment planning, the tooth models of the patient are separated into virtual three-dimensional objects from the scanned dentition of the patient. This can be accomplished using the method disclosed in application Ser. No. 10/626,796, filed Jul. 23, 2003, now issued as U.S. Pat. No. 7,004,754, the entire contents of which are incorporated by reference herein. One skilled in the art would appreciate that the virtual teeth can be represented by shell models or volume solids, or by any other description allowing for a calculation of the distance between two such objects. The method for deriving virtual tooth models including roots is disclosed in application "Method and Workstation for Generating Virtual Tooth Models," Ser. No. 09/834,413, filed Apr. 13, 2001, now issued as U.S. Pat. No. 7,080,979, the entire contents of which are incorporated by reference herein.

From Three-Dimensional Tooth Data"

Furthermore, a jaw model is assumed to be present to give the position of any tooth in a known treatment stage. This can be the malocclusion or any otherwise obtained starting situation. It serves as a reference to set forth an orthodontic set-up.

Tooth Features

Tooth features, such as the cusp tips, marginal ridges, central groove lines, buccal grooves, contact points, etc. play key roles in defining some well established orthodontic treatment planning criteria such as: alignment, marginal ridges, bucco-lingual inclination, occlusal relationships, occlusal contacts, interproximal contacts, root angulation, etc. Indeed, the American Board of Orthodontics (ABO) has introduced an Objective Grading System (OGS) for evaluating the results of an orthodontic treatment once it is completed using these criteria.

Methods for digitally finding the tooth features, such as the tooth axes system, marginal ridges, cusp tips, contact points, central groove lines, and buccal grooves on a virtual three-dimensional model of a tooth are disclosed in application Ser. No. 11/233,623 filed Sep. 23, 2005, pending.

The tooth models must be provided with tooth features like cusp tips, incisal edges of the front teeth, marginal ridges, tooth axes system or root center. In the following description, incisal edges of the incisors are defined as the points situated the most laterally and occlusally on the tooth surface. These points reside on the labial surface for the mandible, on the lingual surface for the maxilla. This definition conforms to the ABO convention.

Figure 2A:
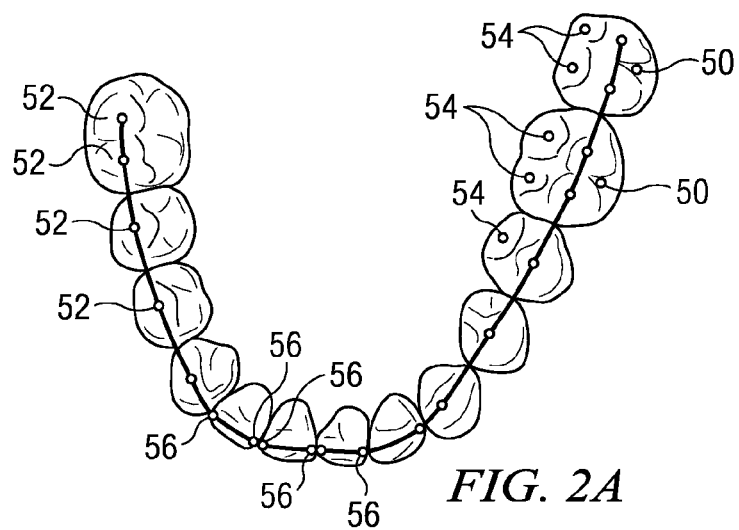
FIGS. 2A and 2B show virtual teeth by shell models in malocclusion of the mandible and maxilla, respectively; as well as some exemplary tooth features.
Figure 2B:
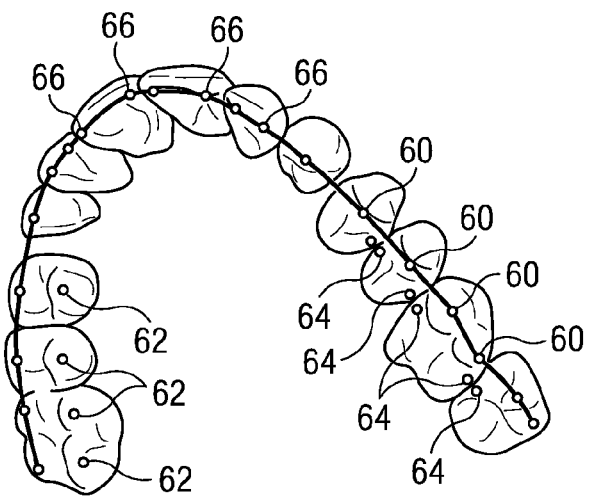

FIGS. 2A and 2B show virtual teeth by shell models in malocclusion of the mandible and maxilla, respectively; as well as some exemplary tooth features. For example, FIG. 2A shows the tooth features such as buccal grooves 50, buccal cusp tips of molars 52, lingual cusp tips of molars 54, and the lateral edges of the front teeth residing on the labial surface of the teeth. Similarly, FIG. 2B shows the tooth features such as buccal cusp tips of molars 60, lingual cusp tips of molars 62, marginal of molars 64, and the lateral edges of the front teeth residing on the lingual surface of the teeth. Spherical shapes are used for illustration purposes to mark the tooth features (characteristic points). For better illustration purposes, lines are used to join the spheres thereby representing the classes of cusp tips and incisal edges. It will be appreciated that the tooth features are found using the methods disclosed in application Ser. No. 11/233,623 filed Sep. 23, 2005, pending, the entire contents of which are incorporated by reference herein.

Division of the Tooth Corrections into Approximately Independent Sub-operations

According to the preferred embodiment of the invention disclosed herein, it is intended to construct the set-up from single sub-operations. The tooth movements induced by these operations should be geometrically orthogonal to each other.

Definition of a Global Reference System

As a first step, a novel global reference system is defined. The global reference system disclosed herein provides a methodology for moving the virtual objects, such as virtual teeth, in a manner that is consistent with the orthodontic principles; and does not cause tooth displacements that were not intended but were caused as a side effect of some planned tooth displacements. One skilled in the art would appreciate that this capability of the global reference system in preventing undesirable, side-effect tooth displacements adds greatly to the quality of the virtual orthodontic treatment planning. It sets the median plane and thus the mirror symmetry of the jaw.

The symmetry plane is important, because for a desired symmetrical set-up its position determines the magnitude of the necessary tooth position corrections to achieve facial symmetry. That means this plane determines the facial midline for the upper and lower jaw.

The global reference system also roughly decides about the position of the horizontal plane and therefore about the vertical direction of any tooth movement. For example, the vertical direction may coincide with the z-axis of the global reference system. Then mesio-distal and vestibular/lingual movements as well as tooth rotation will take place within the x-y-plane of that system.

All tooth movements to form the arch of the upper or lower jaw are situated in the horizontal plane, that is the x-y-plane of the mentioned global reference system. The design characteristics for the arch form are among others factors that shape the outer form of the tooth arch, which determines the necessary rotation for any single tooth, the global width of the jaw and the AP positions of the anteriors and the first molars. Also set in the x-y-plane are the relations of upper and lower jaw that concern the arch form.

The tooth movements to set up the occlusal plane take place along the vertical axis of the global reference system (Curve of Spee), as explained later on.

Figure 3:
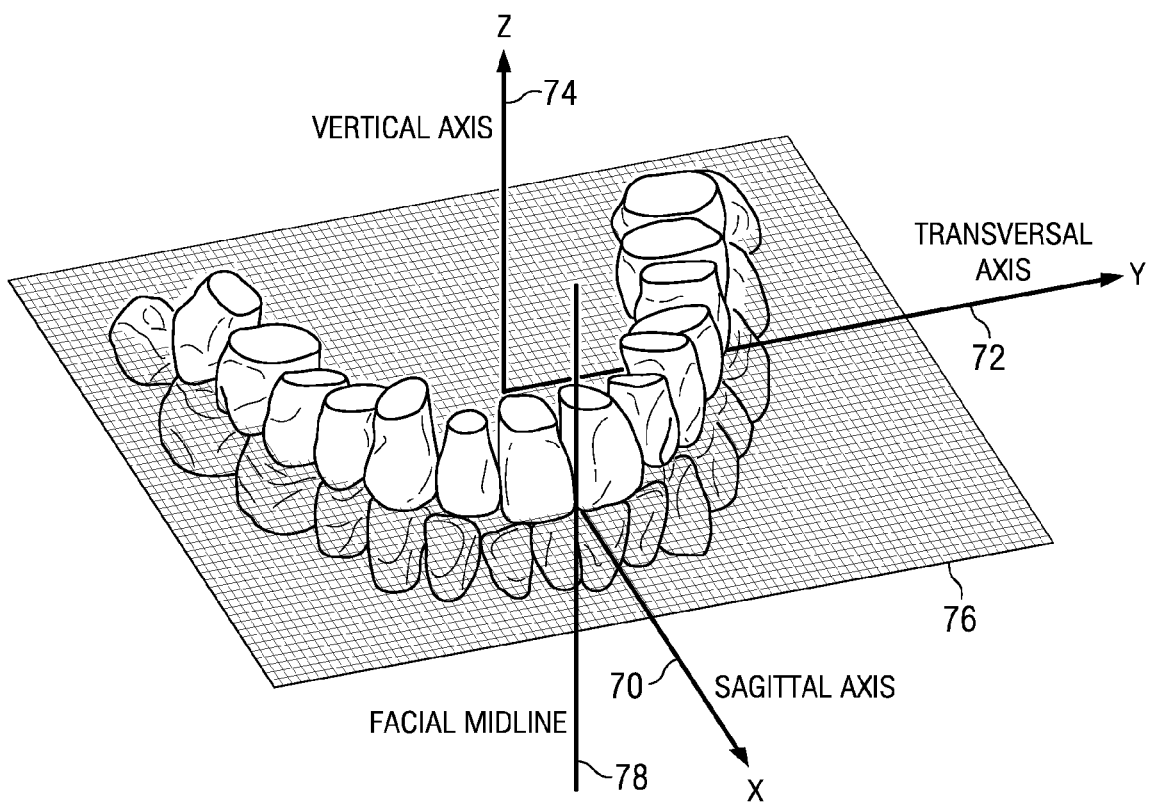
FIG. 3 shows an example of the global reference system comprising the x-axis or the sagittal axis, the y-axis or the transversal axis, and the z-axis or the vertical axis.

FIG. 3 shows an example of the global reference system comprising the x-axis or the sagittal axis 70, the y-axis or the transversal axis 72, and the z-axis or the vertical axis 74. The x and y axes form a horizontal plane 76 which is calculated as a balance between of the occlusal surfaces of the upper and the lower jaws, which are represented here by the respective tooth features. One skilled in the art would appreciate that there are several ways to realize this balance. The x and z axes define the median plane, which is not shown in FIG. 3. The facial midline 78 runs through the incisive contact point of the jaw centrals. This way vertical movements are reduced to a minimum when creating the occlusion.

A symmetrical alignment of the global reference system in the horizontal plane is realized using a selected jaw as a reference.

The facial midline of the reference jaw runs through the incisive contact point of the centrals. Further symmetry is provided by equal distances from the molars to the sagittal axis for the right and the left half of the jaw.

Figure 4:
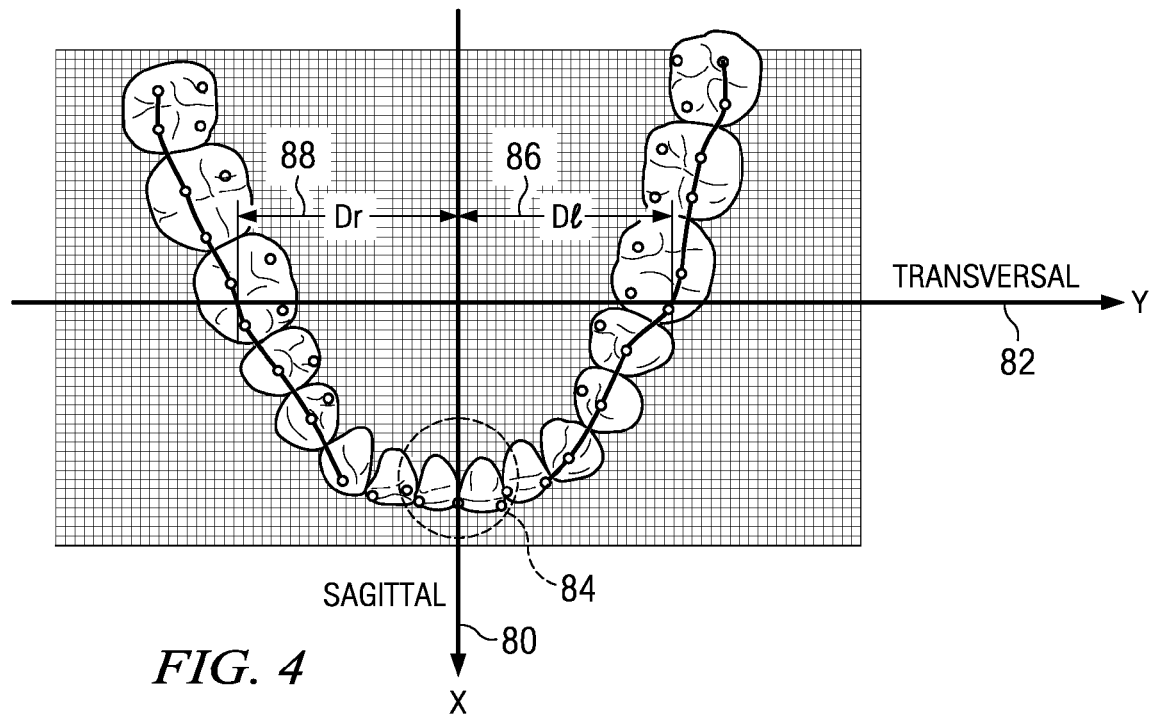
FIG. 4 illustrates an automatic symmetry definition of a reference jaw using a mandible.

The resulting situation is presented exemplarily for a mandible in FIG. 4. It can be recognized that the sagittal axis runs through the centrals and that the molars left and right are equally spaced from the median plane.

This determination is carried out automatically by the system and serves as a suggestion for the user. But it cannot be invariably deduced that the malocclusion positions of the reference teeth used here represent the desired symmetry for the set-up. Therefore the user may have to use the judgment, and corrections as necessary here, that means, he can shift the global reference system to any other position and direction, if he wants to. This feature is enabled by the invention disclosed herein.

FIG. 4 illustrates an automatic symmetry definition of a reference jaw using a mandible. The global reference system is positioned horizontally in a way such that the x-axis or the sagittal axis 80, and the y-axis or the transversal axis 82 are contained in this horizontal plane; and the x-axis or the sagittal axis 80 contains the incisal contact point of the first anteriors 84 and that the distances Dl 86 and Dr 88 of left and right molars to the median plane (sagittal-vertical plane) are equal.

The movement of the tooth roots should also be controlled apart from the already defined directions for horizontal and vertical tooth movement, which also thereby determined the axes for rotation and angulation.

It is intended to move the tooth root center of resistance only vertically and mesio-distally or provide an appropriate force to resist vestibular/lingual movements of the resistance centers. An undesired root movement out of the paradont may be prevented in this way.

This restriction of the tooth movement according to the invention disclosed herein implies a resulting correction of the inclination angle of the teeth when moved in vestibular/lingual direction within the x-y-plane of the global reference system, i.e. the teeth will be tilted.

This constraint for possible tooth movements is implemented by the invention disclosed herein by using a controlled tipping filter for all tooth movements. That means the previously unrestrained torque of the teeth in prior art is now restricted. More details on this topic are provided later on.

Curve of Wilson (Optional). Molar Torque

Alternatively to restricting the vestibular/lingual root movements by the controlled tipping filter, the molar positions can be adapted to a Curve of Wilson. In this case, the controlled tipping filter is deactivated, and the occlusal surfaces of the molars are contacted to a cylindrical face with the cylinder axis being parallel to the sagittal direction. The anteriors and the canines are of no concern for the above discussed procedure.

Instead of a cylindrical face a conical face may be used. Thereby a progressive torque can be realized, the lingual inclination of the tooth crowns will increase in the distal direction.

This operation is facultative and not automatically exercised by the system. It may lead to relevant root movements.

In principle, the form of the alveolar bone could be scanned and 3D measured using suitable CT diagrams and the special form of the parodont could be separated from it. If such records were present, the present model would allow for inhibition of a drift of the roots from the parodont without applying the strict bonding of the roots in the vestibular/lingual direction by the controlled tipping filter.

Relations of Upper and Lower Jaw

The set-up for upper and lower jaw may be created independently or characteristic values for one jaw may be derived from the other. Reference jaws for each, the Curve of Spee and the arch form may be selected.

If the maxilla has been selected as a reference for the Occlusal Surface (Curve of Spee), the properties of that surface are derived from the maxilla and applied to the lower jaw. The vertical balancing of the tooth heights and angulation for optimal intercuspidation of the molars and overbite of the front is oriented at the set-up for the maxilla.

A similar procedure applies if the maxilla has been selected as a reference for the arch form. In this case the set-up for the upper jaw is realized considering the selected or given parameters, whereas the set-up for the lower jaw depends on the set-up for the upper jaw regarding the jaw width, molar class, frontal overjet etc.

So apart from the tooth movements not restricted yet for the single jaws further constraints from the upper/lower jaw relation have to be considered at set-up creation. This will be explained further in the following.

Explanation of the Sub-operations to Generate the Orthodontic Set-up Semi-automatically As mentioned before, the automatic process described in the following paragraphs consists principally of a sequential run of sub-operations.

These sub-operations execute certain tooth position corrections in the different specified directions or principal directions and principal planes of the jaw. They should be designed in such a way that allows for parameterization by independent values for each. The following sections describe these sub-operations and their consequences in detail.

Finding the Alveolar Reference Curve

The task of the Alveolar Reference Curve is the abstraction of the alveolar bone by a smooth planar curve lying parallel to the x-y-plane of the global reference system.

As currently there are no 3D measurements of the alveolar bone present, a simplified method is used to determine the geometrical course of the alveolar bone at least approximately. Its course is deduced from the current positions of the virtual tooth root resistance centers in the malocclusion.

The course of the virtual alveolar bone is represented by the current positions of virtual tooth root resistance centers in the malocclusion or another scanned and 3D measured situation in good approximation. At least it is working for most cases where the teeth are firmly embodied in the alveolar bone.

Even for extreme tooth tilting at least the tooth roots are embodied in the alveolar bone, so that the course of the centers of resistance provides a good approximation to the form of the alveolar bone.

If the latter assumption does not apply with satisfactory significance, manual corrections to the positions of the centers of resistance are possible and advisable.

To construct virtual roots, e.g., the X-Ray absentee diagnosis may be used. The relative size of the respective tooth root may be obtained by scaling the X-Ray image and registration of the 2D relief to the mentioned tooth shell in a suitable 2D projection. The virtual tooth root resistance centers can be approximated by an appropriate analysis of e.g. the length of the transition line between the dentine and the jawbone.

In the same way data from an X-ray CT can be taken to extract their tooth root resistance centers from the separated tooth roots.

Another simple possibility lies in obtaining the position of the centers of resistance from mean value tables of the specific literature and adapt it linearly to the current size of the virtual tooth. This method is surely limited in exactness, but presents an acceptable approximation, since for direction of the tooth motions only relative root movements are of interest or certain directions of motion should be suppressed.

The current model makes use of the last method, but without requiring any changes any otherwise determined center of resistance could be used, so that no limitation is implied.

The virtual tooth root resistance centers are projected into the horizontal plane and then serve to determine the Alveolar Reference Curve.

The resulting 2D point set is approximated by a suitably designed two-dimensional planar balancing curve. As a mathematical basis for the balancing curve various mathematical objects may be used. For example balancing elliptical arches, balancing to parabolic segments, polynomials of higher order or curves of splines of second or third order may be applied. Other curves that are suitable for balancing a two-dimensional ordered point set can be made use of as well.

Here the centers of resistance were approximated by a convex (monotonously curved) quadratic balancing spline. The balancing spline is determined by minimization of the sum of squares of the distances between the centers and the spline, where the convexity is kept as a constraint. The balancing spline shows mirror symmetry relative to the median plane taken from the global reference system.

Figure 5:
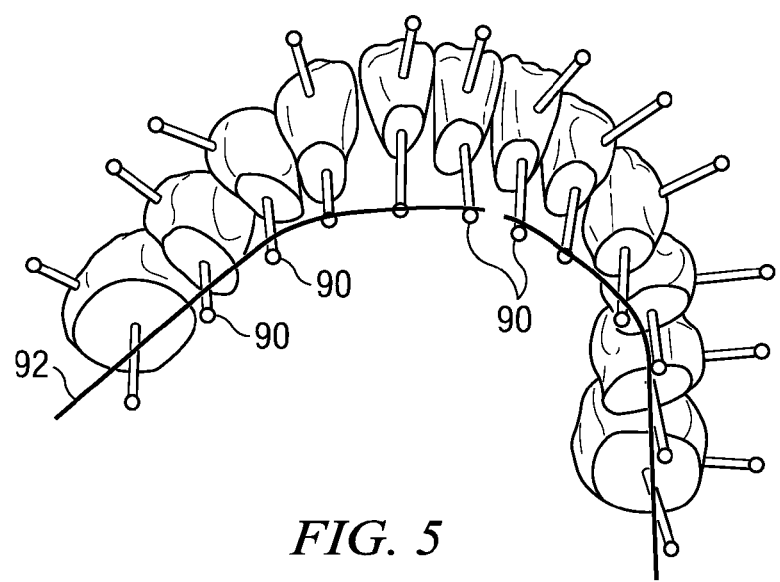
FIG. 5 is an illustration of the representation of the Alveolar bone.

FIG. 5 presents the result of such a calculation. Rods crowned by spheres, which protrude in apical direction from the tooth models, represent the root centers. (The rods protruding in vestibular direction from the tooth models are without concern here.) The balancing spline displayed here as a curve approximates the locations of the virtual tooth root resistance centers. This spline is called Alveolar Reference Curve.

FIG. 5 is an illustration of the representation of the Alveolar bone. This is accomplished through a representation of the virtual tooth root resistance centers using rods crowned with spheres 90. A balancing quadratic spline 92 is placed through the locations of the projections of these centers into the global horizontal plane. It serves as a representation of the alveolar bone.

The Alveolar Reference Curve as well as the 2D horizontal distances between the projected centers of resistance and the curve will be taken down as a set of constants. For illustration see FIG. 6. The distances described are measured in to the normal direction to the spline from the location of the root center.

This set of current distances serves primarily to project the special form of the alveolar bone to the Alveolar Reference Curve. The Alveolar Reference Curve is per definition only as approximation to the form of the alveolar bone and this operation should not induce any root motions.

If he wishes, the user may certainly change this set of distances whereby creating new locations for the root centers in the intended Pre-Set-up.

Figure 6:
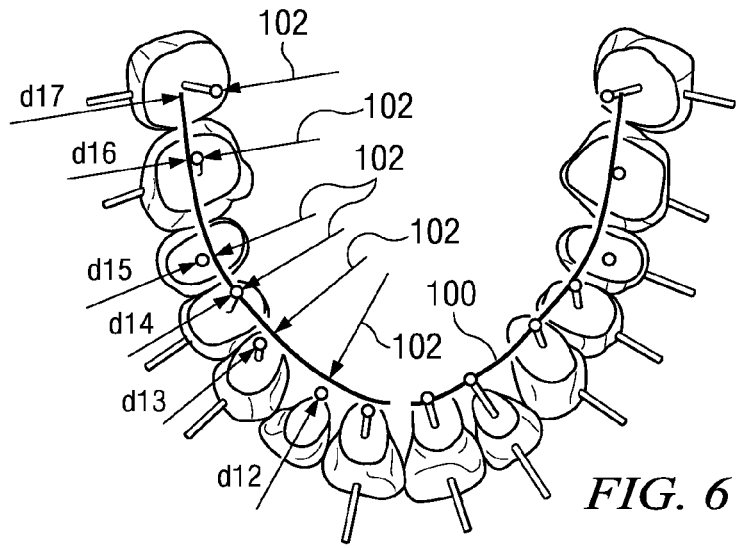
FIG. 6 illustrates the definition of the fixed 2D distances from the virtual root to the spline on a maxillary view from gingival.

FIG. 6 illustrates the definition of the fixed 2D distances from the virtual root to the spline on a maxillary view from gingival. After calculation of the Alveolar Reference Curve 100 the distances 102 from the spline to the projection of the virtual tooth root resistance centers are determined, here as d17, d16, ..., d12, etc. These values are taken down as a set of constants.

Filter of Controlled Tipping

The Alveolar Reference Curve defines the permitted movements for the virtual tooth root resistance centers in a way that allows for vertical motion and motion along the Alveolar Reference Curve without limitation. On the contrary, any motion of the centers of resistance in the direction normal to the Alveolar Reference Curve, that is in vestibular/lingual direction, is excluded.

That means a filter function is realized for the otherwise unrestrained tooth movements to achieve the pre-set-up. The movements are limited to such that will not or only vertically move the centers of resistance out of the alveolar bone.

Figure 7:
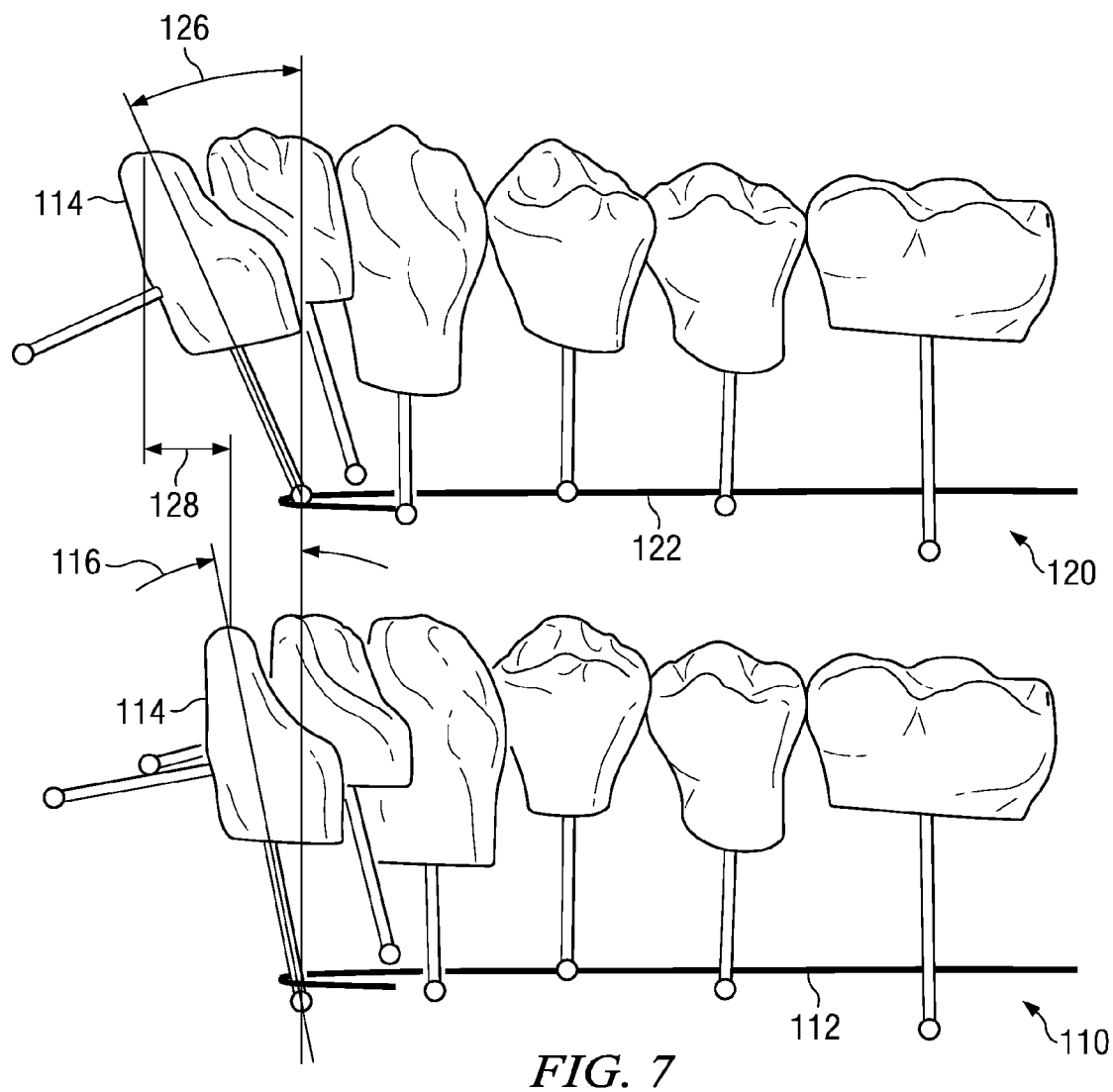
FIG. 7 is an example of the controlled tipping at labial movement of an anterior.
Figure 8:
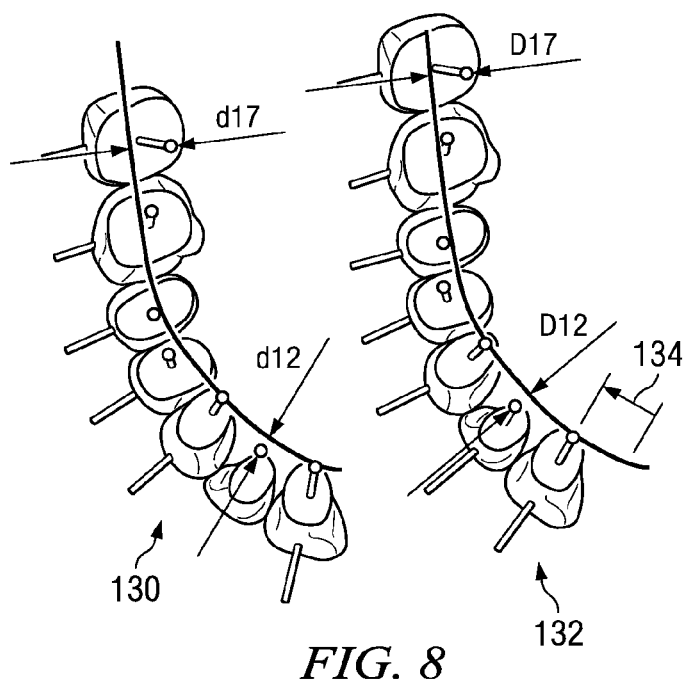
FIG. 8 illustrates workings of the controlled tipping filter on the distal movement of a group of teeth.

FIGS. 7 and 8 present two examples for the effect of the controlled tipping filter. FIG. 7 shows a central cut through the tooth row of a lower jaw as well as the Alveolar Reference Curve and the virtual tooth root resistance centers.

Compared to the situation shown in the lower image half the LR1-central has been shifted in the upper half in the labial direction. It can be recognized that for reason of the bonding of the centers of resistance to the Alveolar Reference Curve the labial motion of the tooth crown also results in a changed torque for this tooth. In relation to the horizontal motion of the tooth crown the root center has been moved a little in the occlusal direction, as there is no limitation for this direction imposed by the filter.

FIG. 7 is an example of the controlled tipping at labial movement of an anterior, illustrated through the controlled tipping of the LR1 central tooth 114. Two views are shown, view 110 with the original position of the tooth 114, and view 120 after tipping the tooth 114. Alveolar reference spline is identified by the reference numeral 112 in view 110, and by the reference numeral 122 in view 120. Angle of inclination of tooth 114 in view 110 is identified by the reference numeral 116, and after tipping in view 120 by reference numeral 126. The labial movement of the LR1 crown resulting from the tipping is identified by the reference numeral 128. Obviously the virtual root center of the LR1-central th at has been shifted in labial direction does not move in this direction. The 2D distance of the center to the Alveolar Reference Curve stays the same. The virtual tooth root resistance center only moves in the vertical direction. The lingual or labial motion of a tooth crown is always combined with a change in the inclination angle of this tooth by this filter, which means the tooth is tipped.

FIG. 8 illustrates working of the controlled tipping filter on the distal movement of a group of teeth. Specifically, FIG. 8 demonstrates the effect of the controlled tipping filter to the mesio-distal motion of the teeth in the distal direction of a jaw half as an example. This figure shows exemplarily the movement of the root reference points at a distal movement of the right half of an upper jaw. The right part presents the jaw segment shifted in distal direction. The 2D distance of the virtual tooth root resistance centers to the Alveolar Reference Curve stays unchanged. The left part 130 presents the group of teeth in their original positions, whereas the right part 132 shows the result after moving the group a certain distance 134 in the distal direction. It can be recognized that the distances d17=D17, d12=D12, and in general dxx=Dxx, indicating that The 2D distance of the virtual tooth root resistance centers to the Alveolar Reference Curve have not been changed after movement of the group of teeth.

For completeness it must be said that the user may at any time be switch off this filter function. Thereby he gains the possibility to readjust manually the positions of the virtual tooth root resistance centers. After reverting to the controlled tipping filter the newly adjusted relative positions are kept long-term.

Parameterization of the Controlled Tipping Filter

This can be accomplished by 2D distance of the virtual tooth root resistance centers from the Alveolar Reference Curve either automatically or manually.

Finding the Occlusal Surface

The occlusal surface is an object that serves to vertically align the teeth. It must be designed in a way that allows for contacting virtual teeth or other objects at one or more relevant surface points to this object.

The relevant tooth points are here the points set off by the tooth feature marks. Particularly useful for the maxilla are the molar marginal ridges, the cusp tips of the canines and the incisal edges of the centrals. For the mandible the buccal cusp tips of the molars are used instead of the marginal ridges. More of this will follow.

Different geometrical forms may characterize the occlusal surface. A level plane, a cylindrical plane, an elliptically formed plane or similar would be possible. The form for the surface will be chosen according to the desired treatment concept. A level surface will lead to an even vertical set-up of the cusp tips, whereas with a cylindrical surface the Curve Of Spee may be considered.

For the actual example, a cylindrical plane was chosen as a basic form. With growing cylinder radius it approximates the level plane.

The automatically generated occlusal surface should be built in a way that it minimizes the distances to the relevant points of the tooth surfaces. The relevant points are different for the upper and the lower jaw. When fitting the occlusal surface to the lower jaw, the cusp tips and the lateral edges of the anteriors are used. For the upper jaw in the molar region the marginal ridges are made use of, in the region of the centrals the incisal edges, which are offset vertically so that the actual contact point of the centrals is shifted by a certain amount in vertical direction.

The position and the radius of the cylindrical plane will be calculated as follows. As a first step a balancing plane is fitted to the relevant points. The position of this plane minimizes the sum of squares of the vertical distances between the plane and the relevant points.

Now another plane is constructed to determine the optimum for the cylinder radius of the final occlusal plane.

To construct this temporary object, the median plane is imagined turned around the x-axis of the global reference system until the normal of the first, balancing plane lies within it.

The relevant tooth points will be orthogonal projected onto thus constructed second plane. To this projection a circle segment is fitted. Again, the sum of squares of the distances to the points is minimized to achieve an optimal fit of the circle segment to the set of projected points. The cylinder axis is obtained from the normal of the second plane at the circle center. The cylinder radius is taken to be equal to the circle radius.

Since it is a task of the occlusal surface to represent the Curve Of Spee for a patient, the mean axes of the cylindrical plane for mandible and maxilla must always reside above the teeth. If a jaw induces another situation, an even plane is automatically chosen as occlusal surface.

Figure 9:
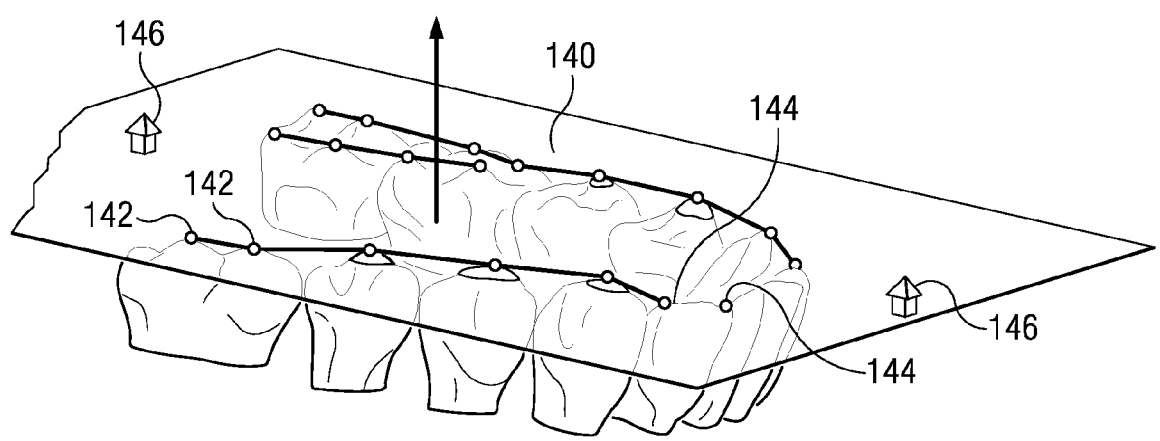
FIG. 9 shows an example of the optimized position of an occlusal surface for a mandible.

FIGS. 9 and 10 show examples of such occlusal surfaces formed and fitted to an optimum to the specific jaw.

FIG. 9 shows an example of the optimized position of an occlusal surface for a mandible. The occlusal surface 140 is displayed in a transparent color. Light points mark the buccal cusp tips 142 and the incisal edges 144. The sum of squares of the vertical distances between the marked points and the occlusal surface has been minimized in order to define the occlusal surface. The control points 146 enable control of the radius of the curve of spee. The occlusal surface is formed here as an even plane, as a fitted cylindrical plane would be curved to the occlusal direction, which is not allowed after the definition of the Curve Of Spee.

FIG. 10 shows an example of the occlusal surface 150 for an upper jaw. The position and the curvature of the occlusal surface has been optimized for a minimum of the sum of squares of the vertical distances between the marginal ridges of the molars 152, the cusp tips of the canines, the incisal edges of the centrals, which are not shown in FIG. 10 for the sake of simplicity, and the occlusal surface. To the distances from the canines and the centrals an adjustable vertical offset has been added, so that the respective teeth protrude clearly from the occlusal surface. Corresponding to the form of the jaw the occlusal surface has been built as a cylindrical plane. Control of the radius of the curve of spee is exercised through control points 154. This accounts for the Curve of Spee for this jaw.

The possibility of specifying a vertical offset to direct the vertical distance between the relevant points and the occlusal surface is of course offered for any tooth if desired.

Vertically Aligning the Occlusal Surface

FIG. 11 shows the result of aligning the teeth to the occlusal surface of FIG. 9. All buccal cusp tips and incisal edges now reside within the occlusal plane. To achieve these final positions, a vertical shift and if required an angulation of the teeth are performed. Specifically, FIG. 11 shows aligning the teeth of the mandible on the occlual surface 160. The front teeth 162 contact the occlusal plane 160 with the lateral edges by angulation and vertical shift. The teeth with two buccal cusp tips contact the occlusal surface 160 by angulation and vertical shift. The teeth with only one buccal cusp tip 166 contact the occlusal surface with the cusp tip by vertical shift.

Figure 12:
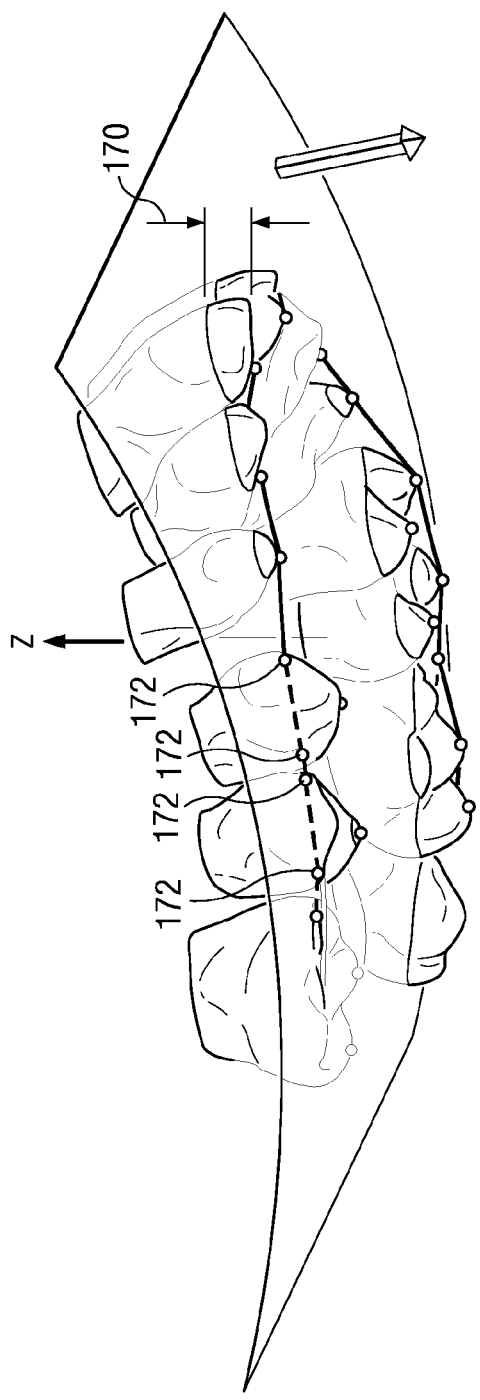
FIG. 12 illustrates the result of aligning the maxillary teeth of FIG. 10 to the maxillary occlusal surface.

FIG. 12 illustrates the result of aligning the maxillary teeth of FIG. 10 to the maxillary occlusal surface. Different from the alignment procedure for the mandible, here the molar marginal ridges are contacted to the occlusal surface by vertical shift and angulation. For the canines and the centrals the cusp tips and incisal edges are used respectively, such as for the mandible. The teeth are just vertically shifted above the occlusal surface after alignment by an offset specified for each tooth. In order to align the teeth of maxilla on the occlusal surface, vertical offset 170 is applied between the lateral edges and the occlusal surface. The marginal ridges of the molar 172 contact the occlusal surface by angulation and vertical shift of the teeth.

The appliance of only one occlusal surface for both jaws plays an important role and requires a special treatment. For this case the molars of the maxilla are automatically adjusted by the alignment to the occlusal surface that their central grooves (represented by the transition line between the marginal ridges) reside at the heights of the molar buccal cusp tips of the mandible. Thus a maximum of intercuspidation has been realized for the molars.

In the region of the anteriors and canines the overbite of the jaw is determined by the mentioned vertical offsets. This value has to be set by the user as a general rule, but it may also come from a default value.

Figure 13:
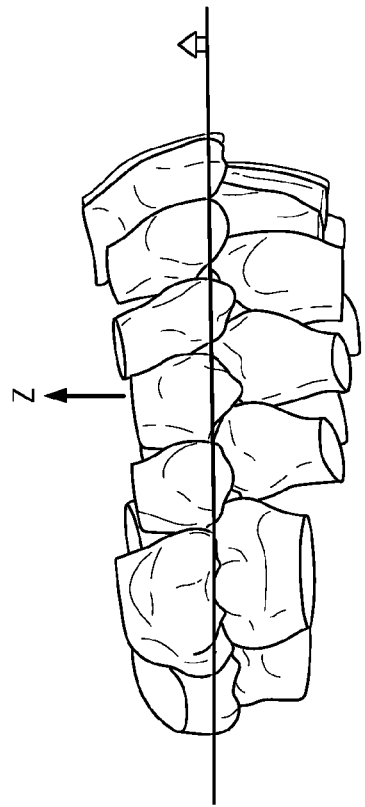
FIG. 13 presents the result of aligning the teeth of maxilla and mandible to the occlusal surface of the mandible of FIG. 9. A view from the right is shown.

FIG. 13 presents the result of aligning the teeth of maxilla and mandible to the occlusal surface of the mandible of FIG. 9. A view from the right is shown.

Figure 14:
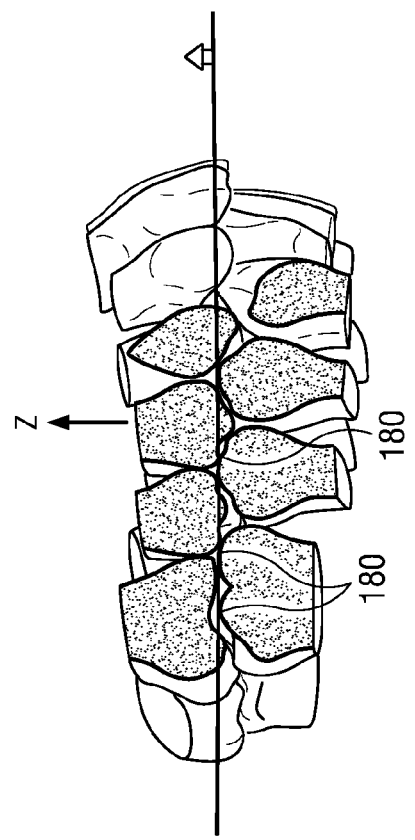
FIG. 14 shows the same representation as FIG. 13. For better illustration the molars have been cut from the right.

FIG. 14 shows the same representation as FIG. 13. For better illustration the molars have been cut from the right. It can be recognized that the cusp tips of the mandible 180 step vertically into, i.e. interfere with the central grooves of the maxillary molars. In case of an arch form fitting to the upper and the lower jaw a good intercuspidation will result.

Figure 15:
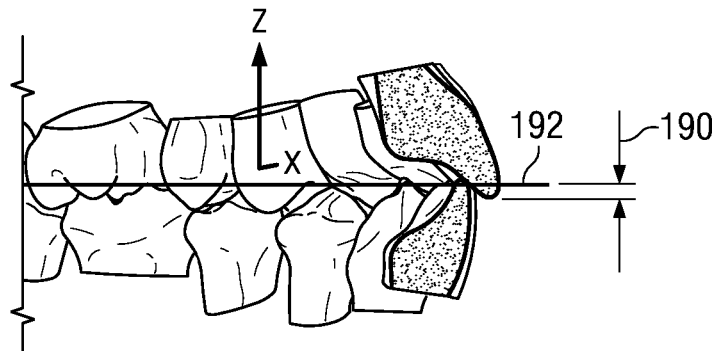
FIG. 15 shows the same representation as FIG. 14, only with the jaw cut at the position of the left central in sagittal direction. It can be recognized that an overbite in the front can be realized by adding the mentioned offsets to the final vertical tooth positions of the front teeth.

FIG. 15 shows the same representation as FIG. 14, only with the jaw cut at the position of the left central in sagittal direction. It can be recognized that an overbite in the front can be realized by adding the mentioned offsets to the final vertical tooth positions of the front teeth. The offset value 190 of the laterals defines the overbite. Here, the occlusal surface 192 is defined as a plane.

The invention disclosed herein offers the following choices.

Parameterization of the Occlusal Surface
(a) Selection of an occlusal surface as a reference
a. maxilla or mandible
b. default or manually
(b) Position of the occlusal surface
a. automatic or manually
(c) Radius of the occlusal surface
a. automatic or manually
(d) Selection of reference teeth to automatically generate the occlusal surface
a. default or manually Parameterization of the Alignment Operation on the Occlusal Surface
(a) Vertical offset values to the anterior positions, overbite of the maxilla
a. default or manually Finding of the Arch Form The arch form is defined as the arch resulting from the projection of the buccal cusp tips of the molars and the lateral edges of the anteriors into the occlusal plane. These points are connected by a smooth planar curve.

Definition of Reference Points:

As a base to generate the arch form a reference jaw (reference tooth positions) is used. It may correspond to the malocclusion or to any in other manner established set of tooth positions, such as after manual corrections to the malocclusion.

The curve may be formed symmetrical to the median plane, which is another possible characteristic.

To obtain a good fit of the curve several alternative ways are possible:

1. Free forming of a symmetrical/asymmetrical convex (monotonously curved) arch minimizing the sum of squares of the distances between the tooth anchors of the reference jaw and the arch to be formed.
2. Free forming of a symmetrical/asymmetrical convex (monotonously curved) arch sticking to or approximating the transversal distance between given reference tooth pairs of the reference jaw, like the first molars, the canines and a central point. This central or mean point is given e.g. by the contact point of the first incisors. Any other combination of reference teeth may be used.
3. By isotropic scaling of a predefined symmetrical arch to approximate the transversal distances between given reference tooth pairs like in 2. above, and a central or mean point. Any predefined arch forms from the specific literature can be applied or used after modification according to the wishes of the treating orthodontists.

Different mathematical objects may represent the arch form. Besides the elliptic or parabolic segments often described in the specific literature e.g. a higher even or uneven polynomial, which approximates for example the mentioned reference points, may be used. These polynomials show a tendency to oscillate, though, and therefore are limited in their use and require a high effort to control.

To achieve an optimum for the fit of the arch form to the reference teeth or for the minimization of the described squares of distances spline representations have proved more efficient. Dependent on the requirements for the tooth arch, there are several ways of proceeding:

1. Regarding the desired convexity of the tooth arch a quadratic spline is recommended. The convexity is given by the mathematically simply enforced positive or negative curving of the parabolic segments between the supporting points. The disadvantage of this spline is the only C1 continuously, though, which means there are sharp bends in the curvature of the arch at the supporting points. Furthermore a quadratic spline shows a minor ability for modulation than a spline of higher order.
2. Regarding good ability for modulation and mathematical simplicity polynomial splines will be chosen, for example splines of third order or their specific representation such as B-Splines, NURBS, Bezier-Splines etc.
3. For minimizing the number of supporting points to be controlled by the user and providing ability for modulation e.g. "splines in tension" can be used. This sort of splines offers the possibility for additional straightening or curving of the segments between the supporting points. Such qualities are shown by the Exponential-Spline, which however does require more calculation time.
4. A free forming capability can be realized by simplified procedures. After choosing a set of reference teeth or an otherwise obtained reference status the spline may only be fitted to these reference teeth. That means the number of supporting points is reduced compared to that for the whole set of teeth. Also this enables to set exact values for certain arch characteristics/parameters such as the molar distance or the canine distance.

But other mathematical models would also be possible.

Definition: The obtained spline is called arch form spline.

Figure 16:
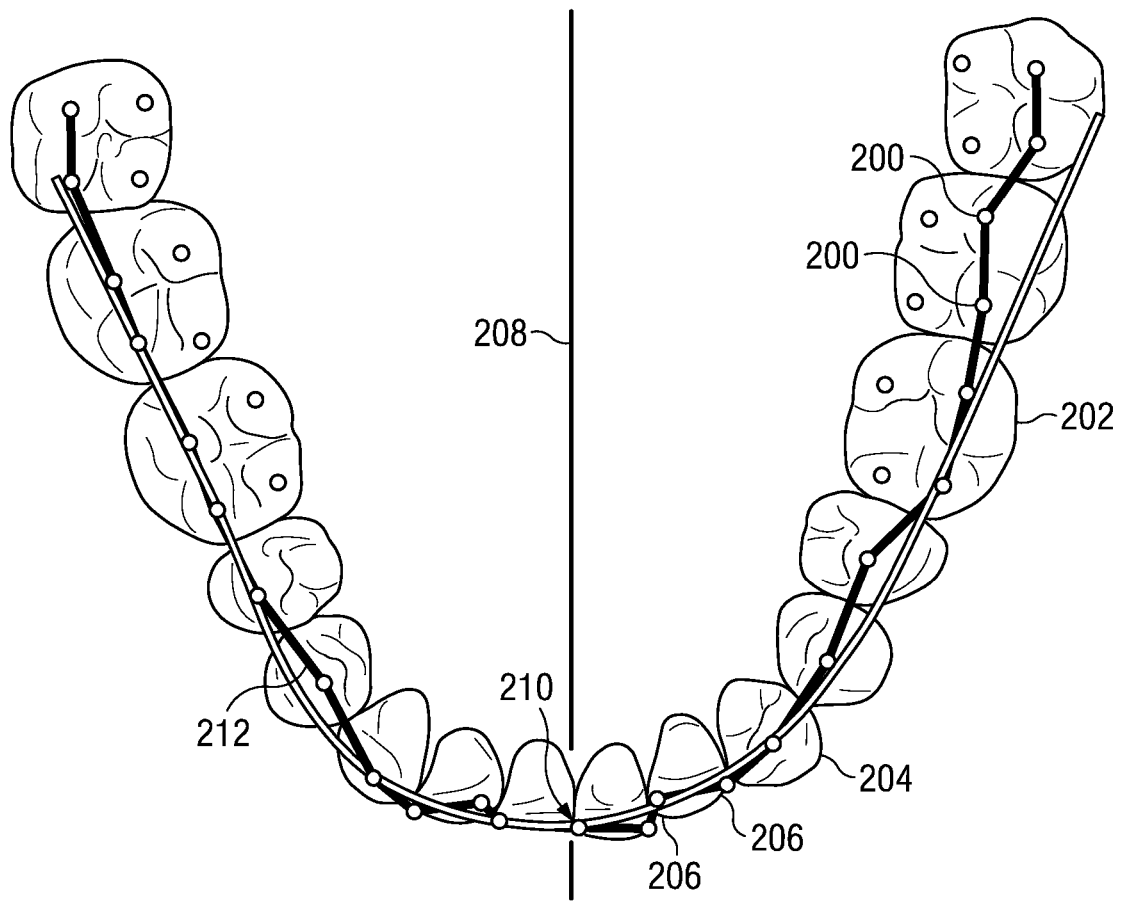
FIG. 16 shows an exemplary construction of an arch form spline on the malocclusion of a lower jaw.

FIG. 16 shows an exemplary construction of an arch form spline on the malocclusion of a lower jaw. The spline shown is constructed so that it represents the horizontal positions of the first molars and the canines as good as possible. In this special case it is formed asymmetrically to the median plain. Here, the sagittal position of the spline is dictated by the incisal edges of the centrals. FIG. 16 shows buccal cusp tips 200, the first molar 202 used to define the width of the arch, canines 204 used to define the width of the arch, lateral edges 206, median plane or the plane of symmetry 208, and the incisal edges 210 that define the sagittal position of the arch. The asymmetrical spline 212 approximates the buccal cusp tips of the molars and the lateral edges of the front teeth.

Aligning on Arch Form Spline

Definition: Tooth Anchor. Every virtual tooth is assorted with a virtual anchor. This anchor is arithmetically realized by a tripod of unit vectors and allows the anchoring of a tooth in the arch form spline. The procedure takes place as follows: the centre of the tripod comes to rest on the arch form spline and one of the vectors of the points into vertical direction. A second vector of the tripod synchronizes with the tangent vector on the arch form spline in the centre of the tripod. This enables the user to move a virtual tooth easily along the arch form spline so that the cusp tips of the tooth follow the shape of the arch form spline during the movement.

Figure 17:
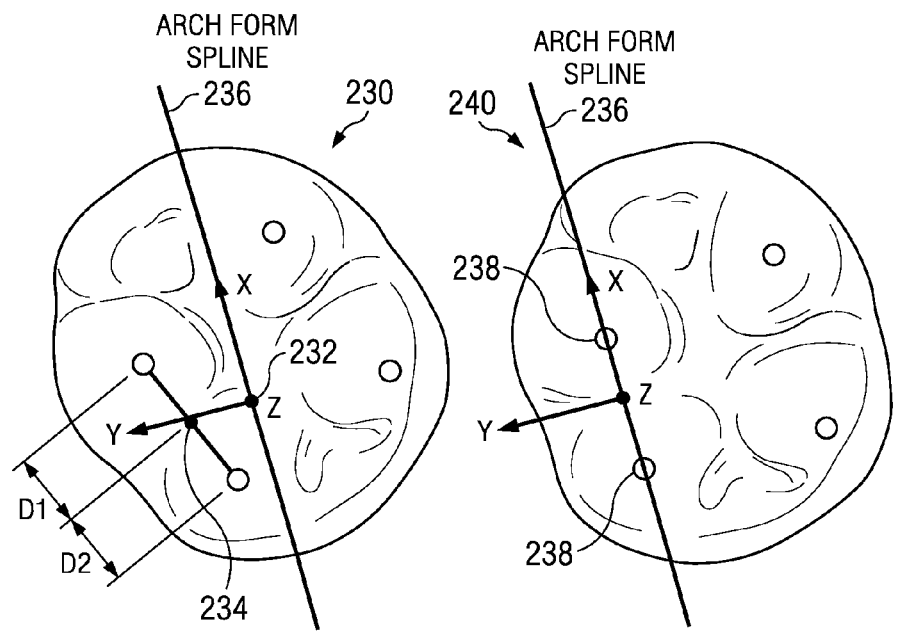
FIG. 17 is a representation of the tooth anchor on a 1st molar of a mandible from the occlusal point of view.

FIG. 17 is a representation of the tooth anchor on a 1st molar of a mandible from the occlusal point of view. On the left side 230 one can see the construction of the tooth anchor 232 in the malocclusion position. The reference point of the tooth 234 lies on half the connecting line between the buccal cusp tips 238, shown for convenience on the right side 240, D1=D2, and lies normally to the arch form spline 236. The tooth anchor is calculated new for every relative position of the tooth to the spline. On the right side one can see the tooth anchor of the same tooth in the align on arch form spline position. Here the tooth anchor and the reference point synchronize.

Figure 18:
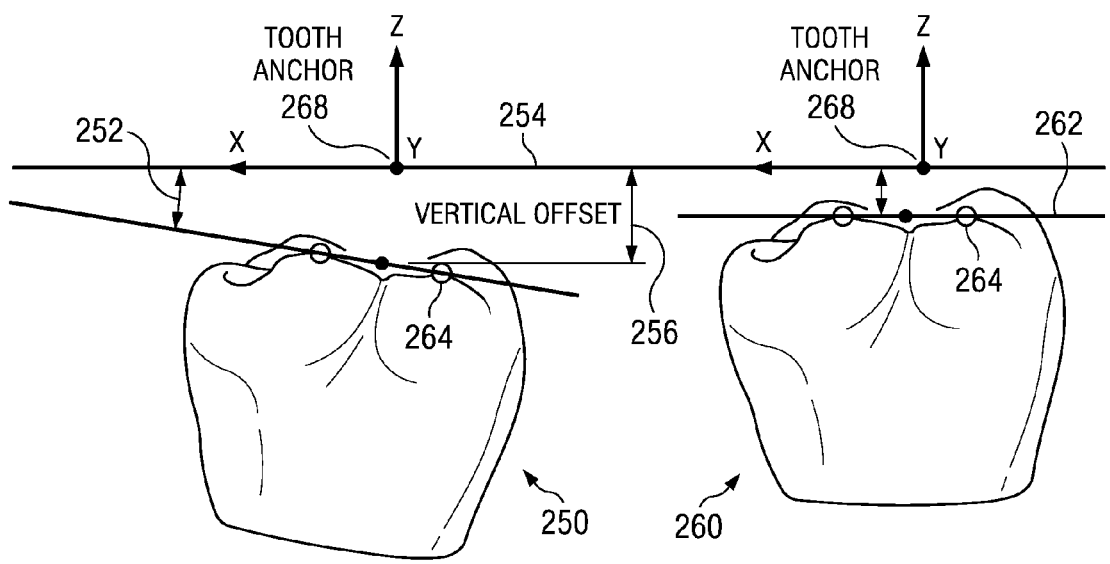
FIG. 18 is a representation of the tooth anchor of the same tooth as in FIG. 17 from the buccal point of view.

FIG. 18 is a representation of the tooth anchor of the same tooth as in FIG. 17 from the buccal point of view. In the malocclusion position 250 of the tooth on the left side of the FIG. 18, the position and alignment of the tooth anchor 268 include the angulation 252 of the tooth, referring to the horizontal plain 254, as well as a vertical offset 256. The right side of the FIG. 18 260 shows the align on occlusal surface position 262 of the tooth. Here the buccal cusp tips 264 lie in the occlusal surface, the angulation of the tooth has been corrected accordingly.

Figure 19:
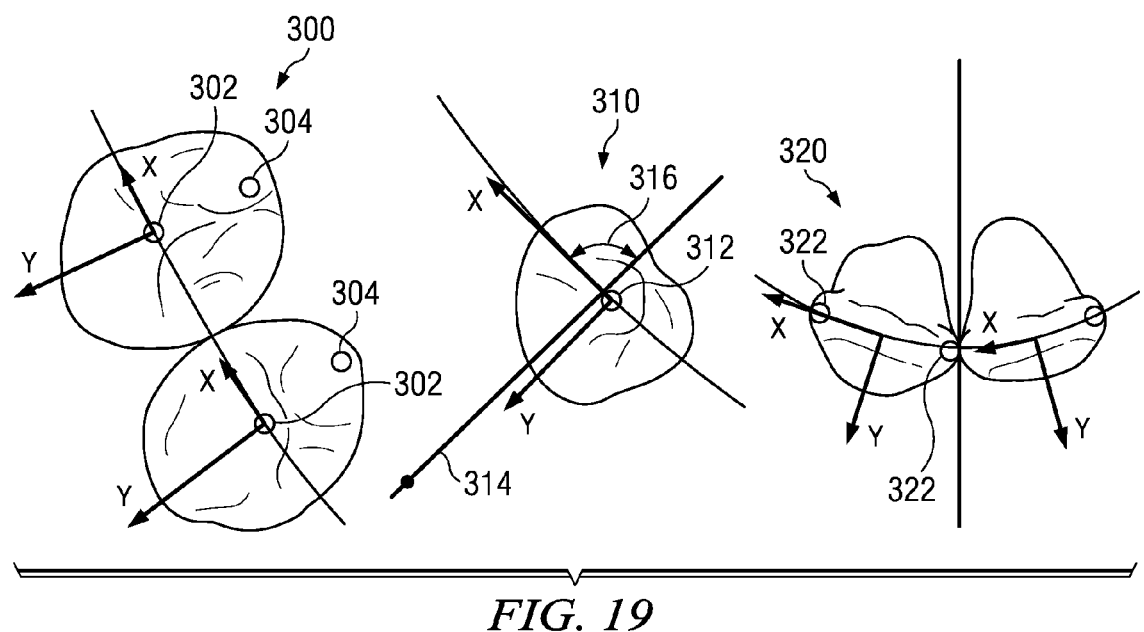
FIG. 19 provides the definition of the tooth anchor of the teeth when aligned on arch form spline position. The reference points of the teeth synchronize in this case with the tooth anchor.

FIG. 19 provides the definition of the tooth anchor of the remaining teeth when aligned on arch form spline position. The reference points of the teeth synchronize in this case with the tooth anchor. The tooth anchor definition for the $1^{st}$ and $2^{nd}$ premolars 300 comprise buccal cusp tips 302 and lingual cusp tips 304. The tooth anchor definitions for the canines 310 comprise the single cusp tip 312, the tooth axis in the vestibular direction 314, and the rectangle between the vestibular tooth axis and x-axis of the tooth axes system. The tooth anchor definition for the front teeth comprise the lateral edges 322.

By using the mechanism of the tooth anchor it is now possible to align the teeth of the pre-set-up along the arch form spline with a possibly desired interproximal distance.

The virtual teeth can be shaped as voluminous compounds or boundaries. Principally every arithmetical representation is imaginable, as long as it allows the definition of the distance between two such objects. In this case a boundary representation is used.

For the alignment of the teeth on the arch form spline, a fixed tooth is presupposed. This fixed tooth is aligned on the arch form spline by the anchor mechanism. This could be e.g. an incisor, whose position on the spline is dictated by the middle position of the front. But it could also be any other optional object, e.g. a middle plain.

Besides this fixed tooth (object) the neighbour tooth is preinstalled in a certain mesiodistal distance. This neighbour tooth can be considered as mobile.

In this position the horizontal distance (in the x-y-plain of the global system) of the mobile tooth to the fixed tooth is investigated.

The anchor of the mobile tooth is now moved by the amount of the investigated distance along the arch form spline. Thia is of course to do with respect to the direction of distance and in case of a given interproximal distance, this have to be considered also.

Now again the distance to the fixed object is calculated and the anchor point of the mobile tooth is corrected accordingly like before.

This procedure will be repeated until the interproximal distance, which has to be abided by, is as precise as desired.

Figure 20:
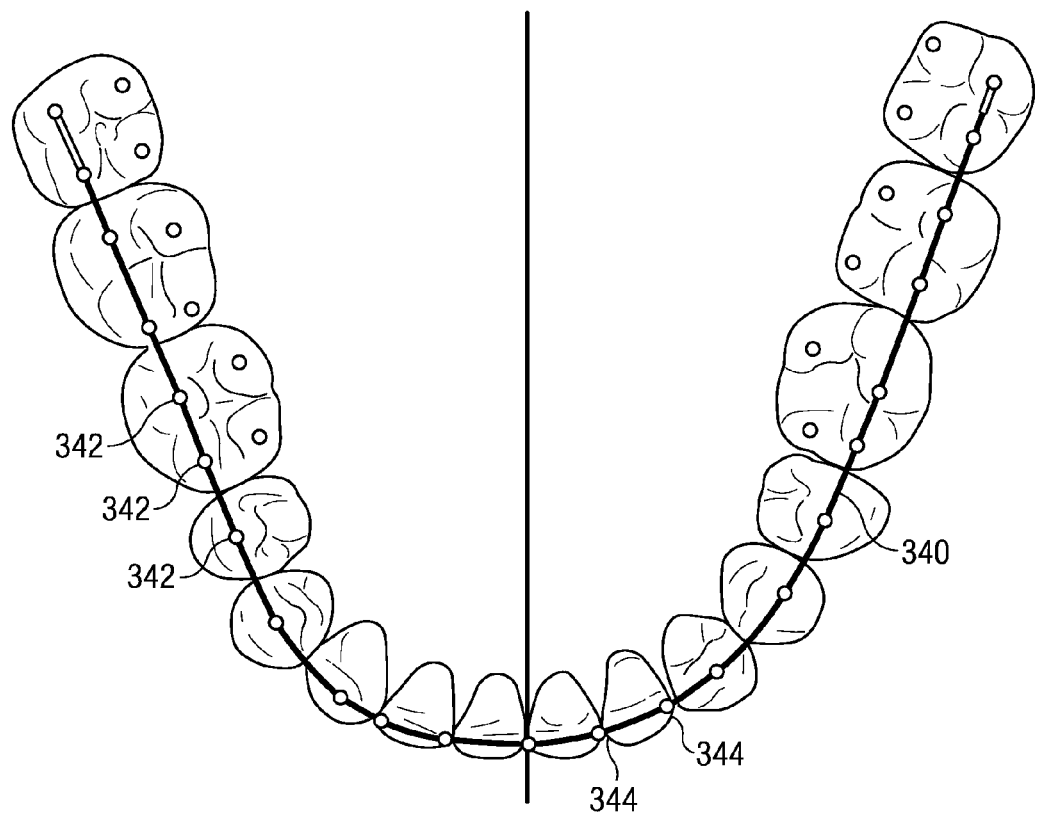
FIG. 20 shows an example for aligning the teeth of a mandible on the arch form spline.

FIG. 20 shows an example for the aligning of the teeth of a mandible on the arch form spline 340. All the significant points (buccal cusp tips and incisal edges) 342 are arranged on the arch form spline without a vertical movement and an angulation of the teeth. The remaining operations which were applied to the teeth are buccolingual and labiolingual movements and rotations around the vertical tooth axes. The teeth are contacted without interproximal distances in this case. The lateral edges of the front teeth 344 are arranged on the arch form spline in view from the occlusal.

Parameterizing of the Shape of the Arch Form Spline

In the preceding discussion, it has been explained how an arch form spline can be defined and created. It has also been mentioned that there are different possibilities for the creation of an arch form spline as a balancing spline. For this, either all the teeth of a jaw or a certain selection of teeth can be used.

Especially the selection of the first molars and the canines is very important.

In this case the positions of the molars and the canines of the reference stages are decisive for the breadth of the arch form and the shape of the arch form. These positions can be manipulated manually in different ways. The corresponding teeth can be brought into the desired position by the navigation of single teeth or the positions of the teeth can be adapted automatically through the application of numeric values for the transversal distances of the teeth.

Another possibility for the manipulation of the arch form spline results from the sagittal position of the apex of the spline.

The apex is determined by the horizontal sagittal position of the first incisors, as shown in FIG. 16. Here are also different possibilities for the manipulation of this position. The first incisors of the reference stages can be manually moved sagittally. Another possibility is to include the sagittal movement of the first incisors automatically through the application of a numeric offset-value.

Figure 21:
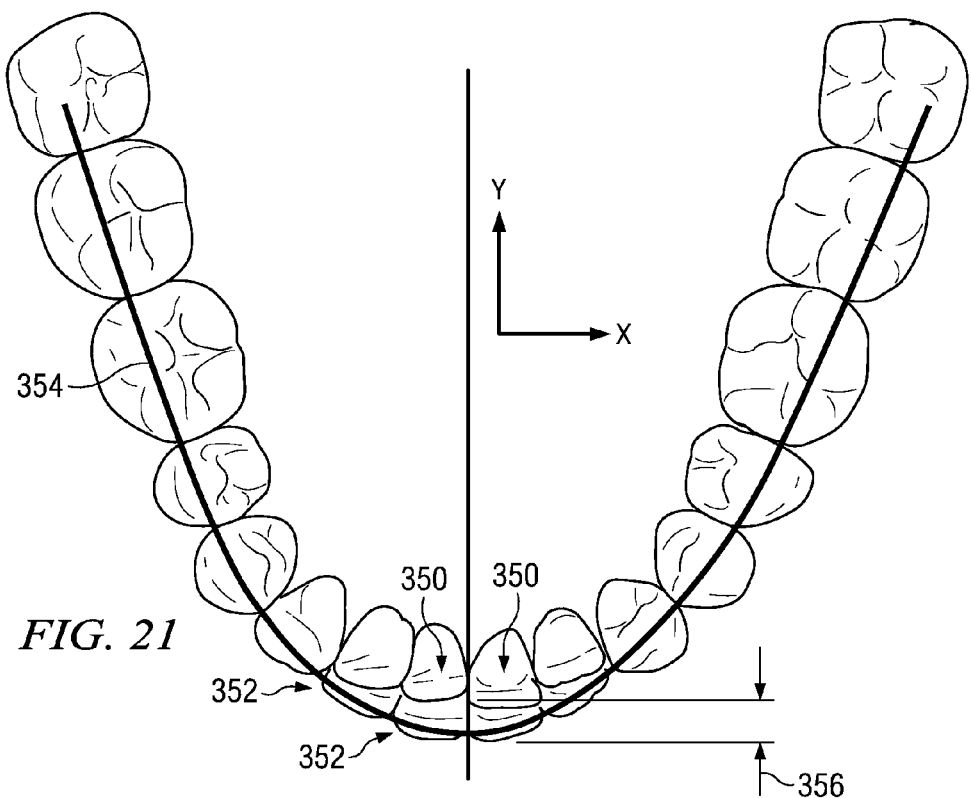
FIG. 21 shows the mandibular teeth in the malocclusion position superimposed with the teeth in the treatment set-up position, along with the desired arch form spline. Offset of the AP-positions of the front teeth is required to remove the crowding.

An example for the effect of this operation is given in FIG. 21. Through the sagittal shift of the first incisors and keeping of the positions of the canines an arch form spline with an extended front segment, compared to the reference stage, is created. A shortened front segment would be created by a corresponding movement of the incisors into lingual direction.

This means during the alignment of the teeth on this spline the incisors move in lingual or labial direction. This initiates e.g. an extension of the front segment with labially moved first incisor positions and a parallel tipping of the front teeth, if desired. Obviously those adjustments could be made automatically under further constrains, as e.g. the avoiding of interpenetrations of the teeth in the front segment. This will be considered later.

FIG. 21 demonstrates the effect of the labial movement of the first incisors on the arch form spline and therefore the development of the front segment of the jaw, in this case a lower jaw. As can be seen easily, the space between the canines (which have been stated as reference teeth here) has extended. The front teeth have more space for the reduction of the crowding. FIG. 21 shows the mandibular teeth in the malocclusion position 350 superimposed with the teeth in the treatment set-up position 352, along with the desired arch form spline. Offset 356 of the AP-positions of the front teeth is required to remove the crowding.

Another possibility to manipulate the arch form spline is to form its shape directly by using the control points. This possibility of shaping the arch form spline can be used besides the other given possibilities of parameterizing, in order to e.g. globally correct the form of a given malocclusion or of a differently achieved reference stage before the automatic process is accomplished.

Figure 22:
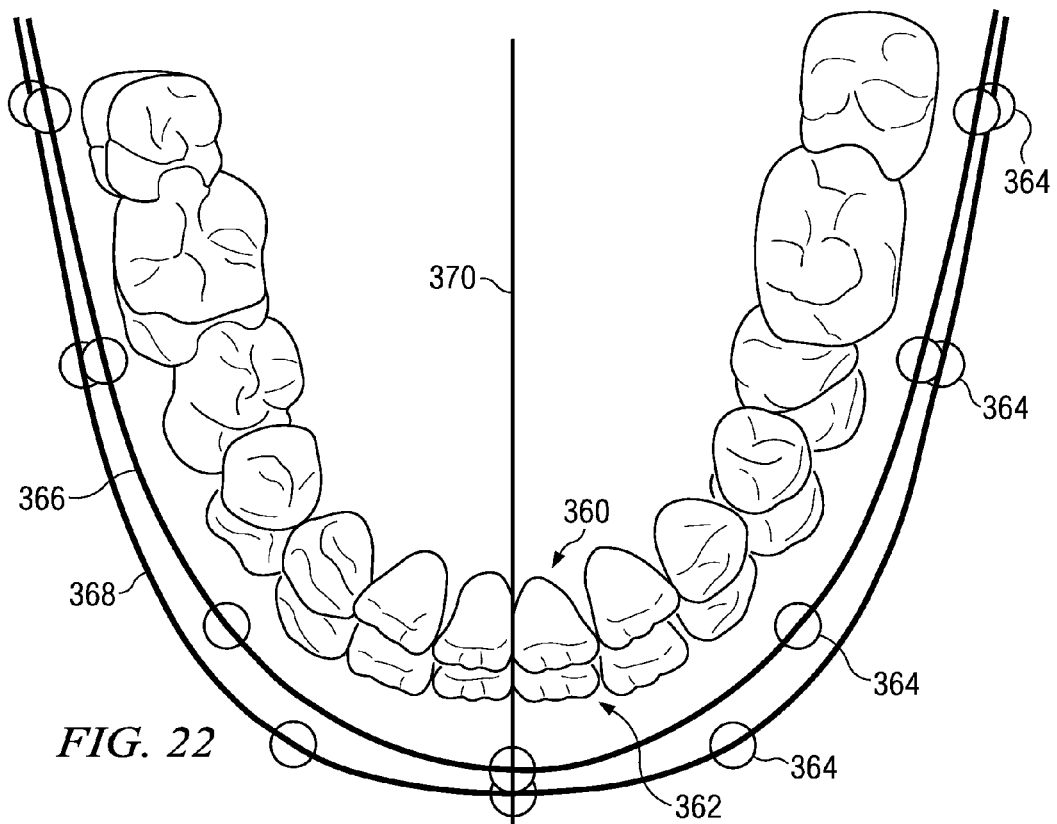
FIG. 22 demonstrates the direct manipulation of the arch form spline by an user during treatment planning.

To demonstrate this manner of proceeding, FIG. 22 shows the overlapping of two different stages of a mandible. The splines are provided with control points which can be moved manually. Furthermore the arch form spline is presented with a certain distance to the teeth for a better manipulation and visibility.

The inner, a little narrower formed spline corresponds to a possible original teeth position (the malocclusion or a reference stage). The further lingually aligned teeth correspond to this spline.

The outward spline demonstrates the arch form spline, after its shape has been changed manually. You can see quite clearly, that especially the control points in the front have been moved sagittally and medially. Consequently a slightly broader form is created in the front and the AP-position of the front has been moved to labial. The slightly more vestibular aligned teeth correspond to the outward spline.

FIG. 22 is only to demonstrate the functioning of the manual formation of the arch form spline. The accomplished manipulation is orthodontically not relevant.

Furthermore, the direct manipulation of the arch form spline is not a necessary operation for the parameterizing of the pre-set-up. It is only mentioned for the sake of completeness.

FIG. 22 demonstrates direct manipulating of the arch form spline by an user during treatment planning. The control points, illustrated as big points, can be selected on the screen and their position in the horizontal plain can be modified by using the mouse. The overlapping lines of teeth demonstrate the alignment on arch form spline for both forms of spline. FIG. 22 displays the original position of the teeth 360 superimposed on the modified position of the teeth 362. The control points of the arch form spline 364 can be used to manually modify the original spline form 366 to a new form 368. Also shown is the median plane 370.

Consequently, the following are the options:
  the distance/position of the molars (automatically corresponding to the reference stage or manually)
  the distance/position of the canines (automatically corresponding to the reference stage or manually)
  offset for the AP-position of the centrals (automatically or manually)
  direct manipulation of the arch form spline (manually)

Deriving of the Arch Form Splines from a Reference Jaw

During the configuration of the arch form and the alignment on arch form spline the reference jaw is examined independently from the dependent arch in each case. During a responding configuration of the arch form and also of the alignment on arch form for the dependent arch, several curvature are however deducted from the reference jaw. Like this, the maxilla mandible relations are taken into consideration or created.

If both jaws have been chosen as independent, they are treated as if both jaws were reference jaws.

The arch form spline for the dependent arch is created similarly to the reference arch. The only difference is the usage of calculated positions instead of the positions of the first molars. These calculated positions result from the demand that the cusp tips of the molars of the mandible should fit into the central grooves of the maxilla. We interpret in this context the connection line between the distal and mesial marginal ridges as the central groove of the tooth in question.

The essential conclusion is, that according to this deduction, the arch form spline of the mandible approximates about the course of the central grooves of the maxilla.

Obviously the arch form spline therefore has to be created always firstly and the teeth of the reference jaw are already aligned before the spline of the dependent arch can be created. This is another fundamental rule for the creation of the pre-set-up. Normally the system obeys to this rule automatically. However, since it is possible to influence the order of the treatment of the jaw manually, the user should explicitly survey the observance of this rule.

Figure 23:
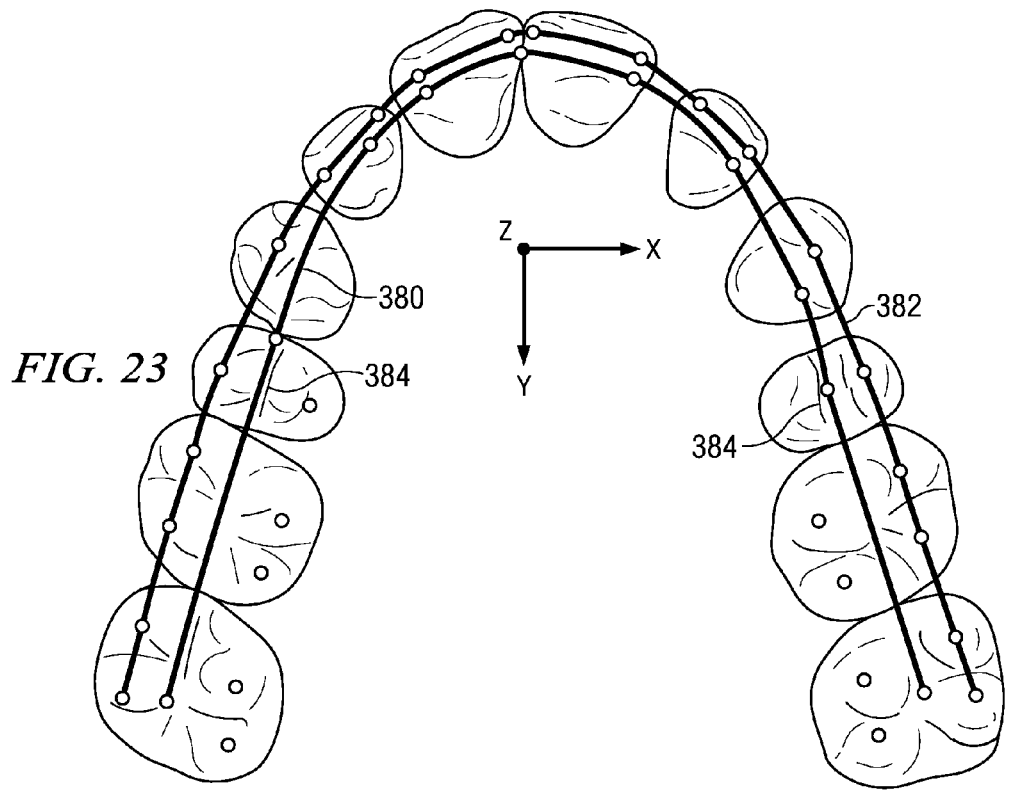
FIG. 23 illustrates elements for deriving the dependent arch form spline from the independent jaw. The illustration includes the arch form spline of the mandible, the arch form spline of the maxilla, and the central grooves of the teeth of the maxilla.

FIG. 23 shows that by using the marginal ridges of the molars of the maxilla as supporting points for the calculation of the arch form spline of the mandible, the arch form spline of the mandible approximates directly the course of the central grooves of the maxilla. FIG. 23 illustrates elements for deriving the dependent arch form spline from the independent jaw. The illustration includes the arch form spline of the mandible 380, the arch form spline of the maxilla 382, and the central grooves of the teeth of the maxilla 384.

Deriving the Breadth of the Dependent Jaw

The deriving of the breadth of the jaw of a reference jaw takes place directly during the calculation of the arch form spline.

To begin with, we have to differ between which of the two jaws has been determined as a reference jaw. In the case of the maxilla being the reference jaw, the marginal ridges of the maxilla will be used as supporting points for the adjustment by the arch form spline of the mandible in the molar section, instead of the anchor point of the mandible.

In this way the arch form spline of the mandible approximates the course of the marginal ridges of the maxilla. During the align on arch form spline operation the buccal cusp tips of the molars move to the spline. Thus the deriving the dependent jaw leads directly to the interference of the cusp tips of the mandible in the marginal ridges of the maxilla from the vertical point of view.

Figure 24:
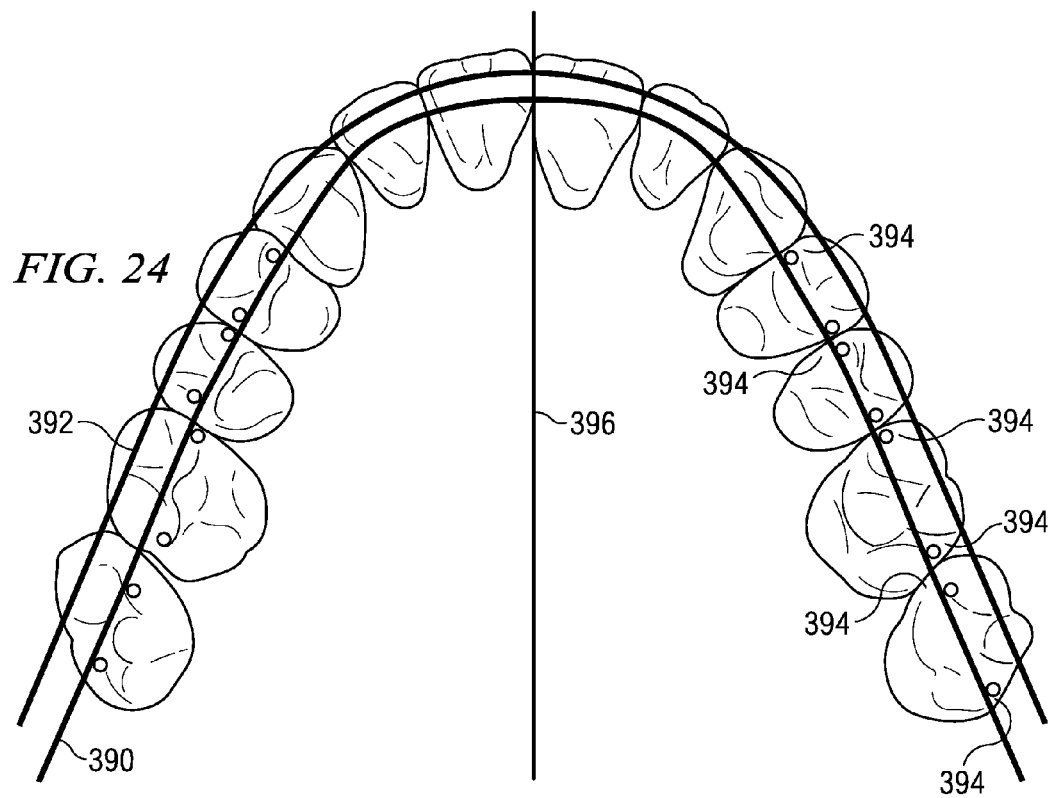
FIG. 24 illustrates elements for deriving the arch width of the opponent jaw from the reference jaw. The illustration includes the arch form spline of the mandible, the arch form spline of the maxilla, and the marginal ridges of the upper molars. Also shown is the median plane.

FIG. 24 shows a demonstration of the deduction of the arch width of the dependent arch from the independent or the reference arch form. In the area of the molars the arch form spline of the mandible approximates the central grooves of the teeth of the maxilla. (In this case the maxilla is the dependent arch. This doesn't matter for the construction of the arch width. If the mandible is the dependent arch, it would lead to the same relations.)

The symmetry of the dependent arch always corresponds with the reference arch and can therefore not be tooled separately. FIG. 24 illustrates elements for deriving the arch width of the opponent jaw from the reference jaw. The illustration includes the arch form spline of the mandible 390, the arch form spline of the maxilla 392, and the marginal ridges of the upper molars 394. Also shown is the median plane 396.

If the mandible is determined as the reference jaw, a modified procedure will be used. Instead of the anchor points of the molars of the maxilla, modified supporting points are used. The supporting points result by adding a buccal offset to the course of the arch form spline of the mandible.

Figure 25:
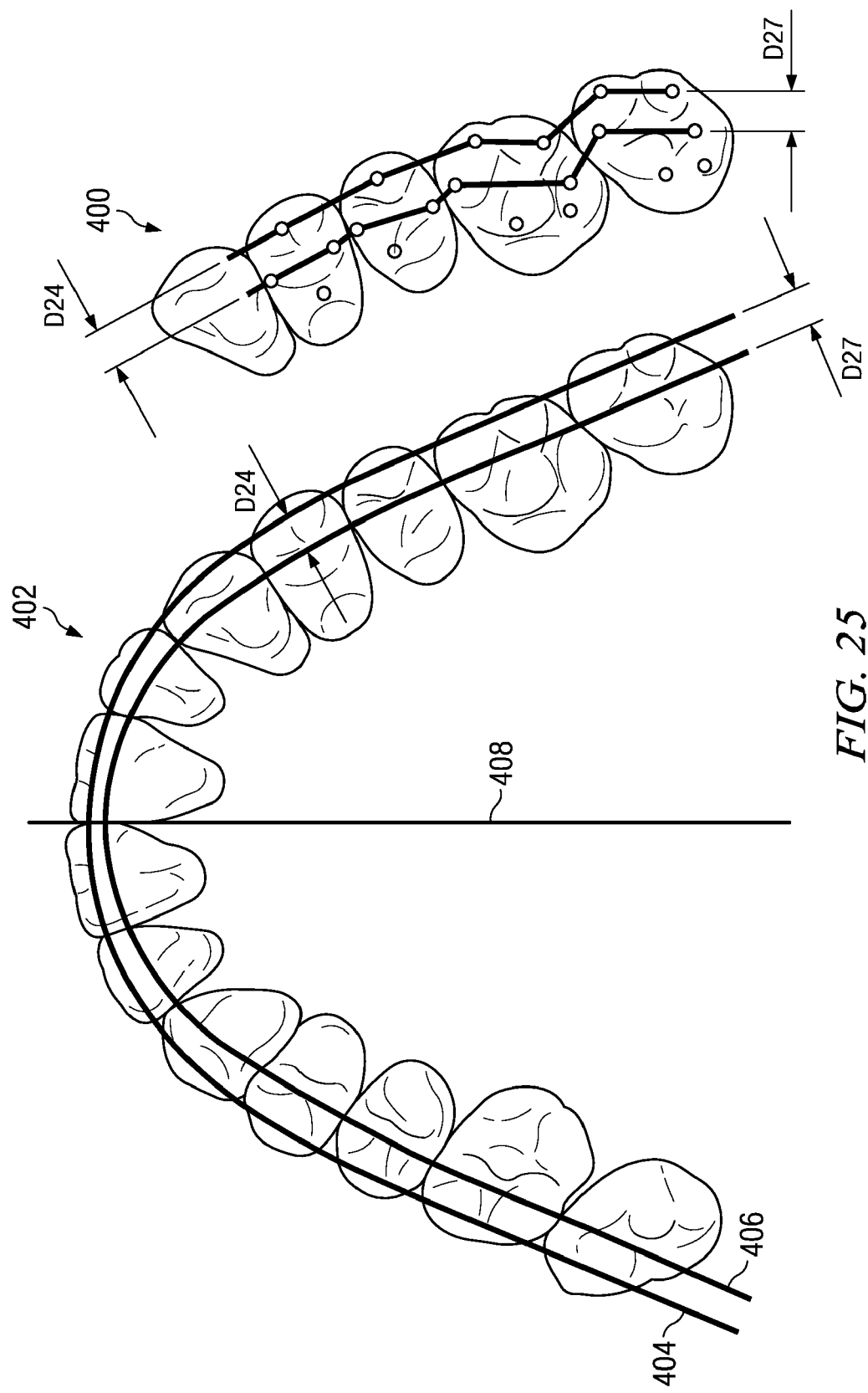
FIG. 25 shows the elements for deriving the arch width of the maxilla from the mandible.

In FIG. 25 this state of affairs is demonstrated schematically. On the right side the situation of the left molars in the malocclusion of the maxilla is illustrated. The horizontal distance between the middle points of the connection lines of the cusp tips on the one side and the distance of the connection line of the marginal ridges on the other side is calculated for each molar. To give an example here the buccal offsets of the first premolars and of the second molars are shown and called D24 and D27.

On the left side of the figure you can see the result of the calculation of the arch form spline of the maxilla. It has been constructed so that virtual supporting points are used as supporting points instead of the cusp tips of the molars of the maxilla. Those are created by adding the buccal offsets mentioned above to the course of the arch form spline of the mandible in the places of the molars of the maxilla.

FIG. 25 shows the elements for deriving the arch width of the maxilla from the mandible. The right side 400 shows the left lateral segment of the malocclusion of a maxilla. For every molar, the horizontal distance between the cusp tips and the central groove is ascertained; here it is marked exemplarily for the first premolar and the second molar. As shown on the left side 402, after the formation of the arch form spline for the maxilla 404, those distances turn up again approximately as the buccal distance between the splines in the places of the molars. Also shown are the arch form spline of the mandible 406 and the median plane 408.

This leads to an alignment of the marginal ridges (central grooves) of the molars of the maxilla with the cusp tips of the molars of the mandible like in the case of the deduction of the arch width of the mandible of the maxilla mentioned above.

Parameterization of the Aligning on Arch Form Operations
AP-Position of the Molars In most cases of an orthodontic set-up, a mesiodistal movement of the molars is not desired, or, if desired, those movements of the teeth should be precisely controllable.

For the aligning on arch form spline this means, that the lateral segments have to be aligned on the spline so that the sagittal positions e.g. of the first molars don't change. This demand can be easily fulfilled automatically by starting with the first molars during the alignment of the corresponding teeth of the segments. These are put into position so that they receive the corresponding sagittal position. The other teeth are then aligned distal and mesial with or without an interproximal distance.

In order to manipulate those positions as a user, only the application of an offset value is necessary. This value is then added to the sagittal position e.g. of the first molars and the procedure continues as described above.

Figure 26:
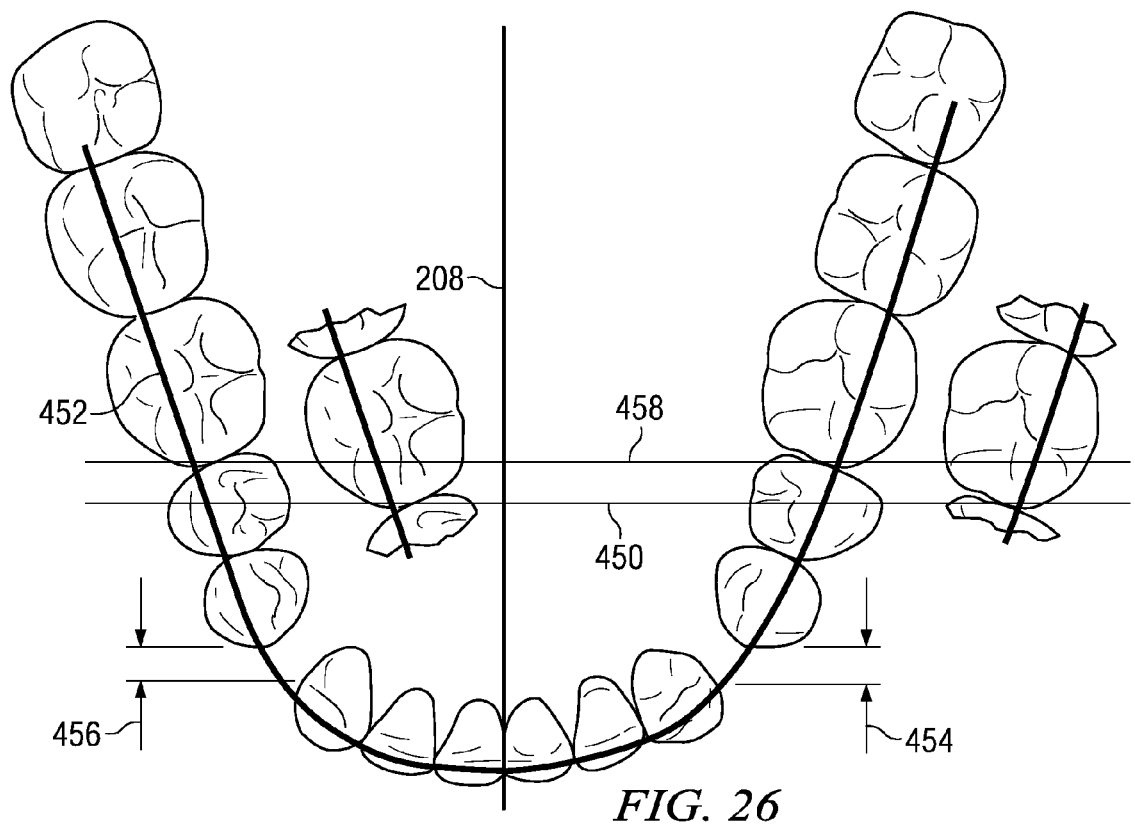
FIG. 26 illustrates a method of getting space by an offset to the AP positions of the laterals of a mandibular.

In FIG. 26 the effect of such an operation is demonstrated schematically. Here the right and the left segments of teeth are both moved distally by a certain amount referring to the reference stage. The original positions of the segments of teeth can be seen e.g. in FIG. 20.

FIG. 26 illustrates a method of getting space by an offset to the AP positions of the laterals of a mandibular. By the distal displacement of the right and left lateral segments of teeth a gap between them and the front teeth has been created. These operations can therefore be used for e.g. the standardization of the AP-positions of the molars. FIG. 26 shows the original sagittal position of the molars 450, the arch form spline 452, the offset to the AP-position of the left laterals 454, the offset to the AP-position of the right laterals 456, and the sagittal positions of the molars after use of the offset for the lateral segments 458.

Interproximal Distances.

Through the procedure of the aligning of the teeth on the arch form spline it is possible to keep any mesiodistal distance between the teeth.

Adjustment of the Frontal Overjet

The adjustment of the frontal overjet takes place entirely analogous to the adjustment of the frontal AP-position of the incisal contact points of the first incisors. Like there, the apex of the arch form spline is brought into the position which corresponds to the incisal contact points of the reference jaw. The desired overjet value is then added to this position. Thereby a positive overjet corresponds to a displacement of the spline apex into lingual direction for the mandible, and to a displacement into labial direction for the maxilla.

By this easy procedure the apex of the arch form spline determines the frontal overjet. After the aligning on arch form spline the incisal lateral edges of the first incisors come to rest exactly on this apex in the horizontal plain. The desired overjet has therefore been realized.

Figure 27:
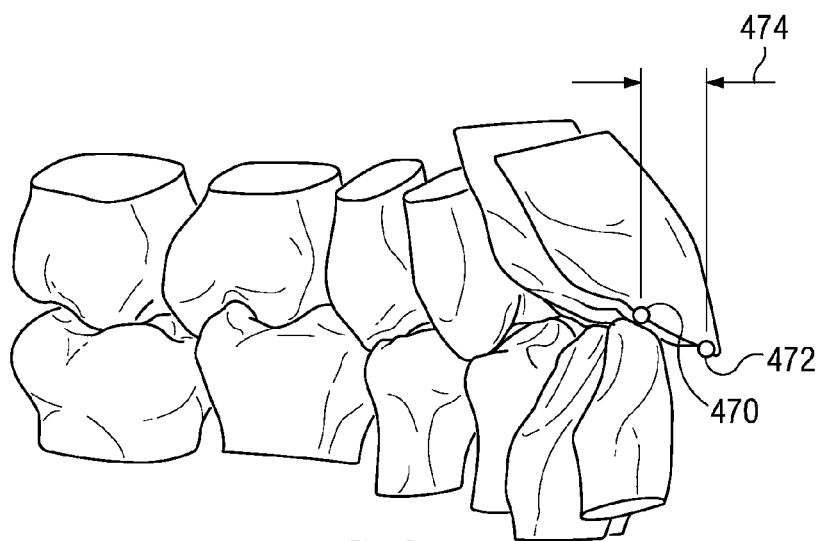
FIG. 27 shows the definition of the frontal overjet as it is used for the automatic configuration of the arch form spline of the dependant jaw.

FIG. 27 shows the definition of the frontal overjet as it is used for the automatic configuration of the arch form spline of the dependent jaw. FIG. 27 shows the incisal contact points of the mandible 470, as well as of the maxilla 472; which in turn determine the frontal overjet 474.

Adjustment of the Molar Relation (Angels Classes)

The molar class can be adjusted separately for the left and right half of the jaw. For the adjustment of the desired molar class, the operation for the displacement of the lateral segments along the arch form spline is used, as demonstrated in FIG. 29.

The lateral segments of teeth are both displaced in distal or mesial direction until the mesio-buccal cusp tips of the first molars align with the corresponding tooth feature of the mandible. You can see the alignment looking at the direction of the normal on the arch form spline.

You have to differ between two classes. For class I, the mesio-buccal cusp tips of the molars of the maxilla are brought into alignment with the buccal groove of the first molar of the mandible. The result of the adjustment of the right side of a maxilla on class I is shown exemplarily in FIG. 28. The buccal grooves of the first and second molars of the mandible are marked by dark points. You can see the alignment of the cusp tips of the molar of the maxilla with the central groove of the molar of the mandible mentioned above.

Through the adjustment of the class, an intersection between the canine and the first premolar has been created. It is the task of the place management on the front segment, which has to be done afterwards, to decompose this intersection.

Figure 28:
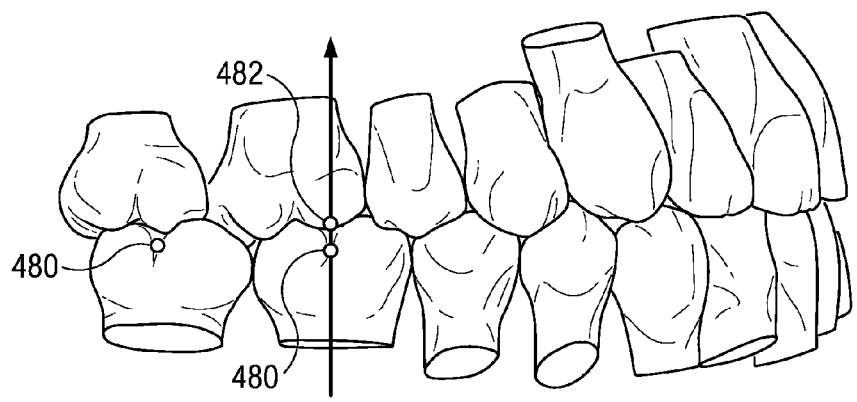
FIG. 28 shows an example of the adjustment of the class I relation by the displacement of the right lateral segment of teeth on the right side of the set of teeth.

FIG. 28 shows an example of the adjustment of the class I relation by the displacement of the right lateral segment of teeth on the right side of the set of teeth. The buccal grove 480 and the mesio-buccal cusp tip of a molar 482.

Figure 29:
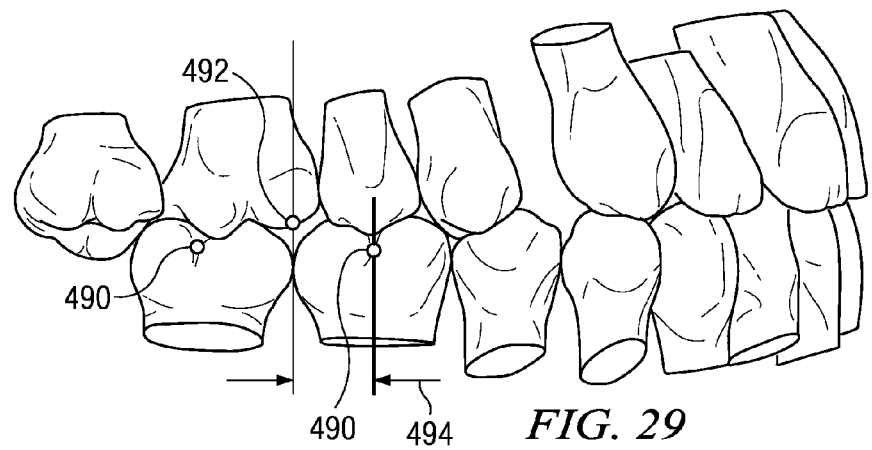
FIG. 29 shows the adjustment of the class II relation for the same set of teeth as shown in FIG. 28 for the comparison purposes.

For the class II relation the mesio-buccal cusp tip of the first molar of the maxilla is brought into alignment with the contact point of the first and second molar of the mandible. Obviously the same procedure as before is used, only the amount of the displacement changes. FIG. 29 shows the result of this proceeding for the standardization of the class II relation for the same set of teeth, as it has already been used for the adjustment of the class I. You can see, unlike before, the great gap, which has been created between the first premolar and the canine.

This gap would have to be closed by the following space management on the front segment in an appropriate way or to be dealt with in any other appropriate manner.

FIG. 29 shows the adjustment of the class II relation for the same set of teeth as in FIG. 28 for the comparison purposes. One can see clearly the created gap between the first premolar and the canine of the maxilla. The elements shown are the buccal groves 490, the mesio-buccal cusp tip of molar 490, and the distal shift of the upper lateral segment.

The adjustment of the class III relation takes place entirely analogous to the adjustments of the other classes. Only in this case the interproximal contact point between the second premolar and the first molar is used as a reference point.

Figure 30:
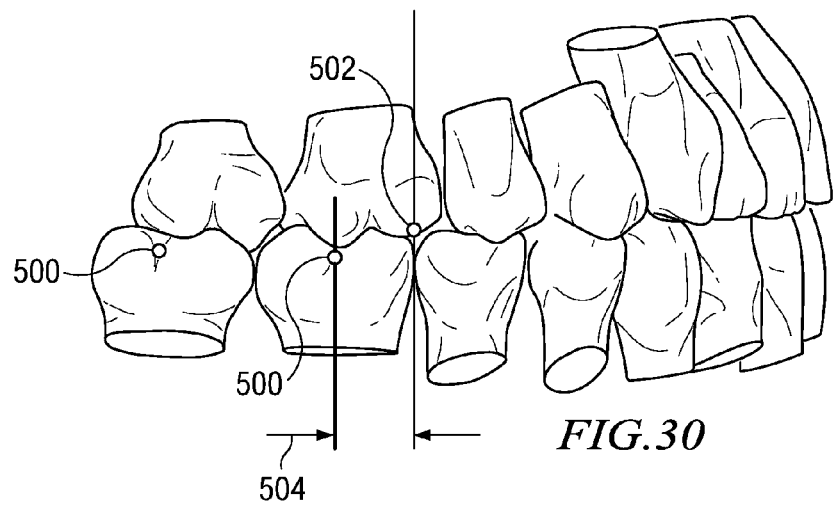
FIG. 30 shows the standardization of a class III relation for the same set of teeth as shown in FIG. 27.

The result is shown in FIG. 30. As you can see this standardization of the classes leads at first to a strong reduction of the space for the front teeth.

In representation in the FIGS. 28, 29 and 30 serve only the demonstration of the proceeding. Their orthodontic relevance for the special case will be left undecided at this point.

Furthermore it should be mentioned that also other molar relations, than those shown here, can be realized (after Angels), e.g. the class relation after Andrews is realized automatically in connection with the align on occlusal surface, that means the corresponding angulations for the vertical adjustment of the cusp tips are calculated with automatically.

FIG. 30 shows the standardization of a class III relation for the same set of teeth as in FIG. 27. One can see the strong intersection of the front teeth of the right half of the upper jaw. The process involves adjusting molar class II on Maxilla. The elements shown are the buccal groves 500, the mesio-buccal cusp tip of molar 502, and the mesial shift of the upper lateral segment.

Midline for the Jaw Specifically Correction of the Global Facial Midline

Figure 31:
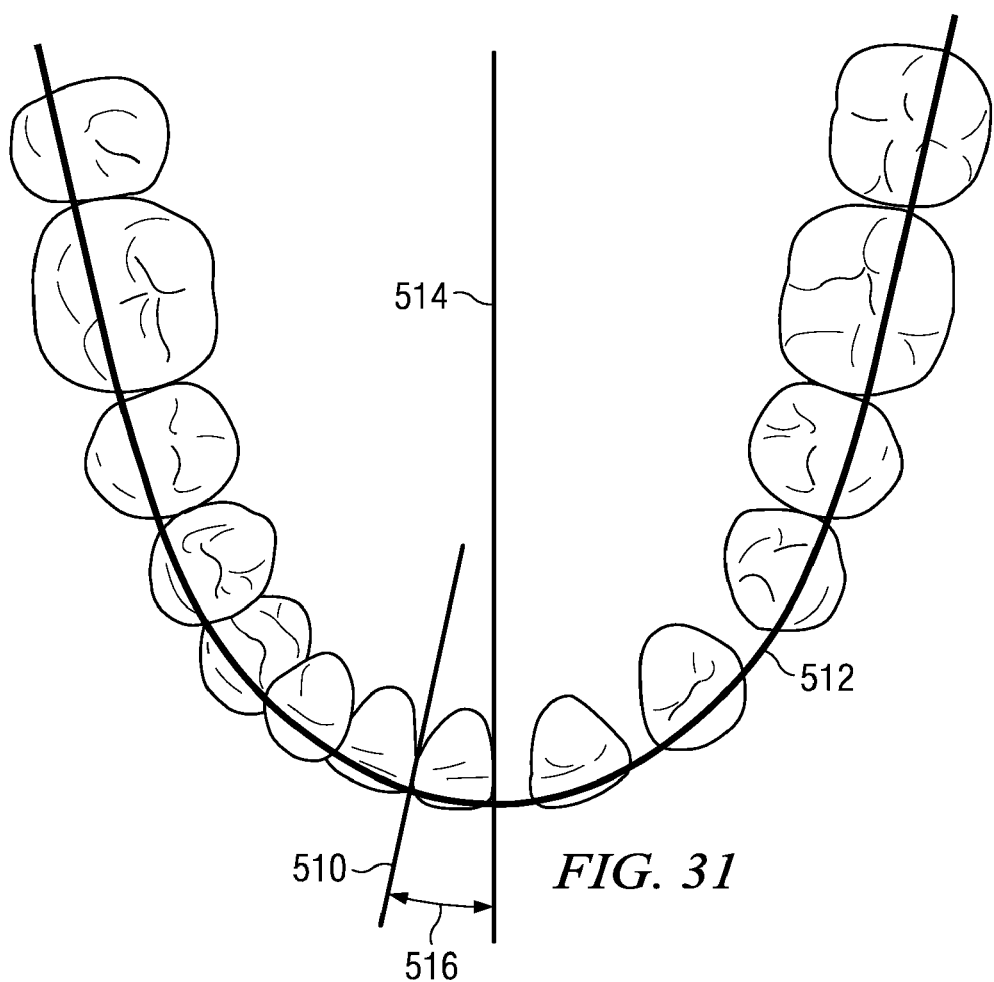
FIG. 31 illustrates the influence of the facial midline object on a mandible. Facial midline object, the arch form spline, the median plane and the length of the bow defining the midline offset value are shown in this figure.

FIG. 31 shows the facial midline as a displaceable even plain, whereby the finite thickness of the plain visible here only serves for better visualization, for the calculation it is a plain without an extension into the direction of the normal.

The facial midline is bound to the arch form spline, that means it always follows the arch form spline during its navigation of the position. The alignment is always orthogonal to the arch form spline.

The midline separates the jaw into the left and right half. Both halves of the jaw have therefore to be regarded as independent during the align on arch form operation.

You can see clearly the effect of the midline: Here the midline has been displaced to the right by some mm. By keeping the AP-positions of the lateral teeth segments, this displacement leads to an intersection of the front teeth on the right side, whereas on the left side clearly visible gaps have been created.

FIG. 31 illustrates the influence of the facial midline object on a mandible. Facial midline object 510, the arch form spline 512, the median plane 514 and the length 516 of the bow defining the midline offset value are shown in FIG. 31.

Concatenation of the Part Operations for the Semi-automatic Creation of the Pre-set-up of a Reference Jaw In the proceeding sections the effects of the single shape parameters have been shown and explained according to the invention disclosed herein. These parameters could have been determined by the user as desired or they can be taken over directly as default values.

This section will show a possible automatic sequence of the usage of the single part operations according to a preferred embodiment of the invention.

1. Activate the controlled tipping filter for all of the following operations
2. Creation of the occlusal surface of the upper and lower jaw by using the indicated reference teeth of the malocclusion or of any other reference stage.
3. Creation of the arch form spline for the reference jaw by using the indicated reference teeth under consideration of the offset value of the AP-position of the front as well as of the desired symmetrical characteristic.
4. Determination of the relative transversal position of the incisal contact points by using the standardized offset value (midline)
5. Aligning on arch form spline. (horizontal correction of the position of the teeth) usage of eventually standardized fixed interproximal distances.
6. Aligning on the Occlusal Surface under consideration of potential offset values for the vertical position of the teeth.
7. Anew aligning on arch form spline in order to correct interferences with the vertical alignment.
8. mesiodistal shift of the lateral segments in order to keep the sagittal position of the first molars e.g. under consideration of a possibly standardized offset value.
9. Adjustment of possibly created interproximal gaps or intersections in the front by the equal distribution of all created gaps or intersections on the individual interproximal space between the teeth on the left and the right half of the jaw.

Optional:

10. Automatic reduction of the interproximal gaps in the front by changing the AP-position of the front under consideration of possibly standardized maximum interproximal reduction values.

The result of these operations is generally a pre-set-up, whose arch width and shape have been performed optimally, as well as the adjustment of the cusp tips of the molars and the incisal edges of the front teeth and the vertical alignment of the teeth on the occlusal surface.

However, the space management in the area of the front teeth has generally stayed unclear. After the automatic process normally interproximal gaps have been created here. Under the indicated constrains for the creation of the pre-set-up, especially under observance of the determined position of the facial midline of the jaw, there is no more degree of freedom for the automatic accomplishment of this unaccomplished space management in the front. Here the decisions of the user are generally necessary.

The user has the possibility to e.g. minimize or annul the resting interproximal gaps by a virtual slurring of the lateral surfaces of the teeth in accordance with a corresponding clinical indication. The interproximal reduction is realised in the mentioned manner of realization by negative interproximal gaps, that means it leads to a directed interpenetration of the teeth at the corresponding points. It is of course also imaginable to demonstrate the slurring of the teeth through a suitable virtual reduction on the used teeth objects. That would mean, new virtual teeth are installed for the teeth to be slurred.

Furthermore there is the possibility to adjust the arch form again by changing the parameters, e.g. the expansion or reduction of the jaw front by vestibular displacement of the canines.

After possibly accomplished modifications of the parameters, the automatic process is started again, which leads to the creation of an accordingly accommodated pre-set-up. A great advantage of the chosen parameter set is the usage of indications for the description of a jaw, which are usual in the clinical every day life.

Principally the automatic process is designed so that it can be used iteratively. That means, the pre-set-up created after one passage of the automatic process can always be used again as a reference stage for a new passage of the process. The convergence of such iteration to is guaranteed, that means without modifications of the parameter set or manual navigation of the teeth or other objects, it will always lead to the same result.

Concatenation of the Part Operations for the Semi-automatic Creation of the Pre-set-up of the Dependent Arch.

The semiautomatic process for the configuration of the pre-set-up deducting from the creation of the pre-set-up of the reference jaw is composed similarly to it.

The main difference to the process for the creation of the pre-set-up of the reference jaw is, that the width of the jaw is not standardized after the malocclusion or any other given reference stage of the currently regarded jaw, but it is explicitly accommodated to the width of the reference jaw. By this, an optimal intercuspidation of the molars is achieved.

Furthermore the AP-positions of the molars and of the front deduct from the reference jaw, that means the desired molar classes and the overjet of the front will be adjusted according to the reference jaw.

This leads to the following sequence of part operation as a possible realization of the process, according to another preferred embodiment of the invention:

1. Activate the controlled tipping filter for all of the following operations.
2. Creation of the occlusal surface of the upper or lower jaw by using the indicated reference teeth of the malocclusion or of any other reference stage.
3. Creation of the arch form spline for the dependent jaw under consideration of the width of the reference jaw and of the AP-position of the front according to the desired frontal overjet. The symmetrical characteristic of the dependent jaw corresponds to that of the reference jaw.
4. Determination of the relative transversal position of the incisal contact points using the standardized offset value.
5. Aligning on arch form spline (horizontal correction of the positions of the teeth) Usage of possibly standardized fixed interproximal distances.
6. Aligning on the occlusal surface under consideration of possible offset values for the vertical position of the teeth (vertical correction of the positions of the teeth)
7. Anew aligning on arch form spline in order to correct interferences with the vertical alignment.
8. Mesiodistal shift of the lateral segments for the standardization of the desired molar class.
9. Adjustment of possibly created interproximal gaps or intersections in the front by the equal distribution of all created gaps or intersections on the individual interproximal distances on the left and the right half of the jaw.

Unlike to the process for the creation of the reference jaw, here the part operation 10 is not available. This is because the observance of the frontal overjet demanded for the dependent jaw and the parallel expansion or reduction of the frontal area exclude each other.

In the connection of the process realised here, the automatic process for the dependent jaw will be accomplished again after the modification of the frontal area. Like this it is guaranteed that the frontal overjet corresponds to the standardized value at any time.

Alternative Possibilities for the Configuration of the Process

Besides the processes for the automatic creation of an orthodontic pre-set-up demonstrated above, other sequences of the part operations are imaginable.

For example, an operation can be used for the approximation of a curve of Wilson. Or the order of the partial operations can be changed if necessary.

It is also imaginable, to e.g. extend the automatic space management in the frontal area, so that the positions of the canines are also corrected. Like this, gaps or intersection between the front teeth could be avoided through the usage of the created expansion or reduction of the jaw additionally. As a result e.g. the dependent jaw could be included in an automatic process of the space management, since further possibilities for the configuration of the offset would be created.

Principally all further correction can be included by iterative usage of the automatic process. By this iteration the reciprocal influence of the positions of the teeth, as they correspond to the partial operations, would be annulled.

For example, the aligning on occlusal surface for a tooth which has been moved horizontally is no longer correct with a curve of spee at hand. Continuous usage of the aligning on occlusal surface operation would correct such an error without modifying the positions of the teeth, which have not been moved.

It depends on the desired exactness, with which the intended positions of the teeth or the global quantity shall be achieved, whether such a possible iteration or the continuous usage of the part operations will be used. On the other hand there is of course the accomplishment of the usage. The compromise which is optimal for the user can be fulfilled in any case.

Occasionally there will be the demand only to treat one jaw, whereas the other one should not be corrected. This doesn't constitute a problem to the deduction of the jaw to be treated from the other one, because the Ok/UK relations rely on tooth features. Consequently the processes for the single jaws can also be used independently from each other. Of course the virtual teeth of the jaw not to be treated and their tooth features have to be at hand.

Another possibility for the configuration of the whole process is created, when the role of the reference jaw and the dependent jaw are swapped after one or several iteration steps. By this e.g. the part operation 10 of the reference jaw process for the space management in the front can be used for the previous dependent jaw. The previous reference jaw then becomes the dependent jaw, whose pre-set-up is now accommodated to the new frontal shape of the reference jaw.

The fundamental concept of using a jaw as reference jaw in order to deduct the dependent jaw from it, referring to specified figures, which is demonstrated here, is not imperative. By using the process for reference jaws for both jaws, completely independent pre-set-ups of the maxilla and the mandible are created.

Support of Orthodontic Surgery Cases

The support of orthodontic treatments like e.g. maxilla or mandible prognathism/retrognathism is also possible.

Example for the Creation of a Pre-set-up

Now, the exemplary result of the automatic process for the configuration of an orthodontic pre-set-up will be demonstrated. Additionally the scenario in which the process has been parameterized will be demonstrated.

Figure 32A:
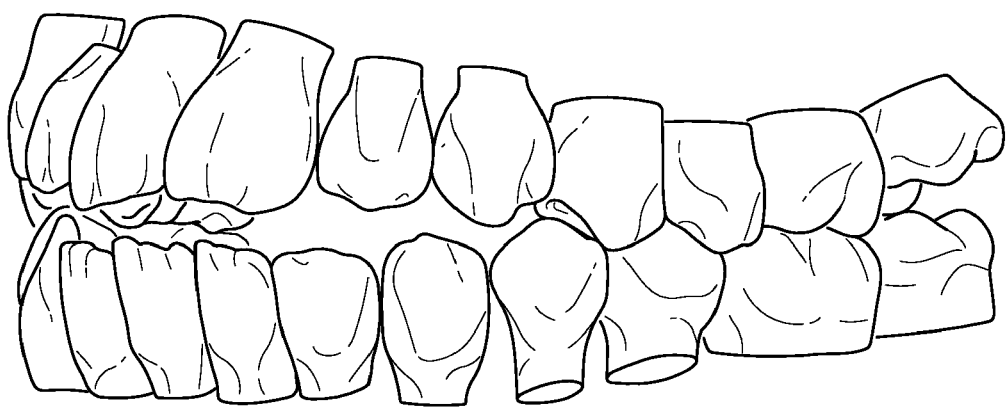
FIGS. 32A and 32B show the malocclusion of an open bite case from labial-buccal left view, and labial-buccal right view, respectively. A treatment planning pre-set-up for this case is illustrated using the invention disclosed herein.
Figure 32B:

In FIGS. 32A and 32B the model of a typical case of a set of teeth with an open bite is shown. You can see in this model that a good class I relation is already given and should be kept. In the front of the lower jaw there is a slight crowding, which should be corrected. On the whole, the bite shall be closed.

FIGS. 32A and 32B show the malocclusion of an open bite case from labial-buccal left view, and labial-buccal right view, respectively. It is desired that for this case a treatment planning pre-set-up be made using the invention described herein.

In FIGS. 33A-33D the semiautomatic created pre-set-up is shown from different points of view.

The pre-set-up has been created with the default parameter, whereby the lower jaw has been selected as reference for the arch form as well as fort he occlusal surface. The arch form shall be formed symmetrically to the median plain.

The used default parameters are:

| PARAMETER | UPPER | | LOWER | |
|---|---|---|---|---|
| | LEFT | RIGHT | LEFT | RIGHT |
| Reference arch for the occlusal plane | | | X | |
| Shape of the occlusal plane | | | plane | |
| Reference arch for the arch form | | | X | |
| Arch shape | Natural | | Natural | |
| Arch symmetry | symmetrical | | symmetrical | |
| Midline | Derived from malocclusion | | Derived from malocclusion | |
| Molar distance | Derived from malocclusion | | Derived from malocclusion | |
| Canine distance | Derived from malocclusion | | Derived from malocclusion | |
| AP-position of Front | | | 0.0 | |
| AP-position of 1st molars | | | 0.0 | 0.0 |
| Class | one | one | | |
| Overbite | 1.0 | | | |
| Overjet | 0.0 | | | |

| For the independent jaw | |
|---|---|
| Parameter | Value/status |
| Arch form | Natural |
| Symmetric/asymmetric | Symmetric |
| Midline | 0.0 mm |
| AP-Position of front | 0.0 mm |
| Molar distance right | Derived from Malocclusion = 27.6 mm |
| Molar distance left | Derived from Malocclusion = 27.3 mm |
| Canine distance right | Derived from Malocclusion = 15.8 mm |
| Canine distance left | Derived from Malocclusion = 15.6 mm |
| AP-Position of the first molar right | 0.0 mm |
| AP-Position of the first molar left | 0.0 mm |
| Vertical offset | Zero for all teeth |

| For the dependent jaw | |
|---|---|
| Parameter | Value/type/derived from |
| Arch form | Natural (every time) |
| Symmetric/asymmetric | Symmetric |
| Midline | 0.0 mm |
| Overjet of front teeth | 1.0 mm |
| Molar distance right | Derived from independent jaw = 28.0 mm |
| Molar distance left | Derived from independent jaw = 28.4 mm |
| Canine distance right | Derived from Malocclusion = 17.6 mm |
| Canine distance left | Derived from Malocclusion = 18.5 mm |
| Molar class right | Class I |
| Molar class left | Class I |
| Vertical Offset/Overbite | Centrals: 1.0 mm |
| | Sec. Inzisors: 0.5 mm |
| | Canines: 1.5 mm |
| | All other: Zero |

Afterwards it showed that a lack of space had occurred in the front through the decomposition of the crowding in the frontal area while the AP-positions of the front and the molars had been kept.

The canines of the upper jaw of the malocclusion are pointing too much into lingual direction because of the lacking contact with the teeth of the lower jaw. This lead to a too big narrowness of the upper arch form, a lack of space in the front occurred and a penetration of the upper laterals with the lower laterals took place.

The lack of space in the front of the lower jaw has been decomposed automatically by the accomplishment of operation 10 described earlier. This lead to a correction of the AP-position of the front by anterior 1 mm. A slight tipping of the front teeth has been created, which was acceptable.

The upper jaw has been deducted automatically again from the unmodified lower jaw. Afterwards the parameter of the transversal distance between the canines of the maxilla has been raised and the automatic process for the maxilla has been started again.

In the result however it showed, that because of keeping the facial midline, little gaps rest between the left front teeth.

Through a slight and regular displacement of the midline of both jaws to the left and a following re-accomplishment of the automatic process for both jaws, the satisfactory pre-set-up shown here has been created.

The proceeding explanations of the single steps for the creation of the pre-set-up shown here are supposed to show exemplarily, how a usual session for the creation of a pre-set-up would be for the user. For this, the automatic process is used in two ways.

In the first step a first proposition for the treatment is made by the automatic process using the default parameter set or a parameter set which has already been modified. After this step the first contradictions in the given parameters mostly become already clear.

In the further steps the automatic process serves for the direct usage of the corrected parameter set. That means, the user can see directly in what way his applications influence the pre-set-up. If modifications of the parameter set are created by the automatic process, they are of course taken over instantly and are at the user's disposal.

Of course the described process can be changed so that the user doesn't have to decide, whether the automatic process is restarted or not. This could always happen automatically, when one of the parameters has been changed.

Furthermore a direction is imaginable, for which all parameters, as far as possible, are done by the mouse, by the usage of the movements of the geometrical positions of the objects visible on the screen, teeth or helping objects, e.g. the midline, which belong to or determine them.

The automatic process could then actualize immediately all teeth positions. For the user this means that he can follow the dynamic formation of the jaw or the modification of mandible-maxilla relations as a reaction to his applications.

Figure 33A:
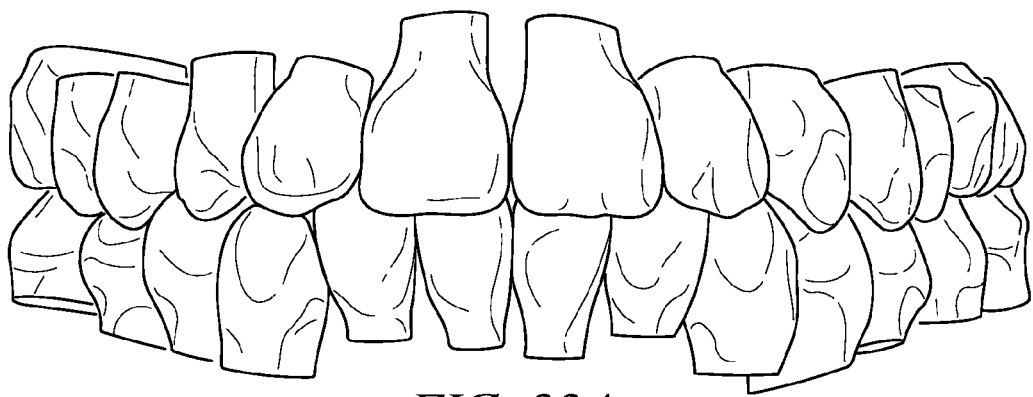
FIGS. 33A-33D show the treatment pre-set-up created by the automatic process disclosed herein from different viewing points.
Figure 33B:
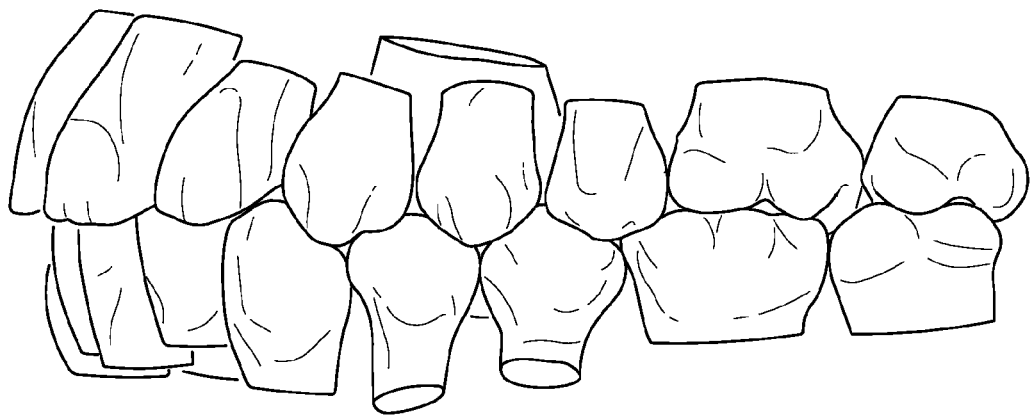
Figure 33C:
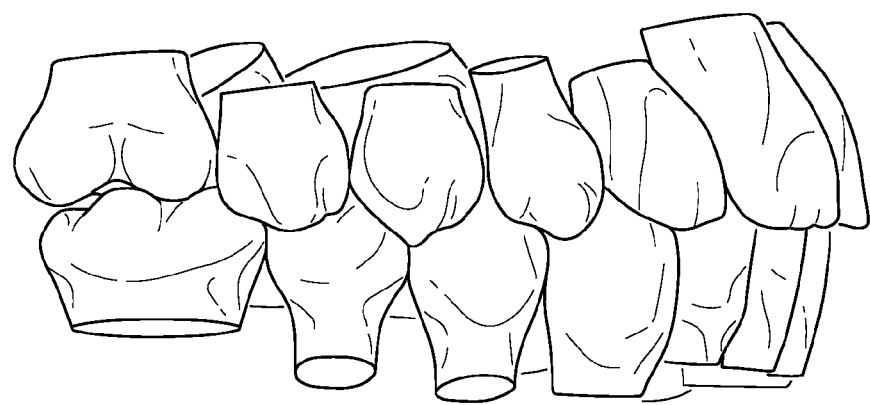
Figure 33D:
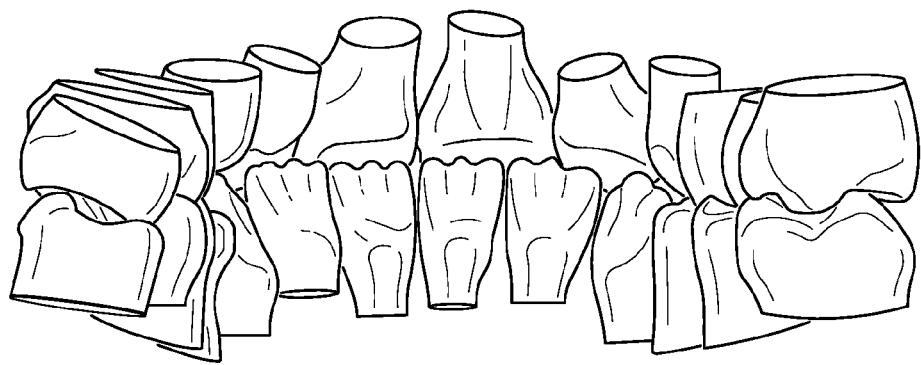

FIGS. 33A-33D show the treatment pre-set-up created by the automatic process disclosed herein from different viewing points. FIG. 33A shows the treatment pre-set-up from the labial view. FIG. 33B shows the same pre-set-up as in FIG. 33A from the left buccal point of view. FIG. 33C shows the same pre-set-up as in FIG. 33A from the right buccal point of view. FIG. 33D shows the same pre-set-up as in FIG. 33A from the lingual of view. In FIG. 33A, one can see the overbite of the front teeth as well as the aligning on the midline of both jaws. In FIG. 33B, the intercuspidation of the molars is visible, as well as the observance of the class I relation of the molars. In FIG. 33C, the intercuspidation of the molars is visible, as well as the class I relation of the molars. In FIG. 33D, the class I relation of the molars has also been adhered to.

Fine Tooth Movement

Like demonstrated in the explanations above, the automatic process and its parameterization relies only on the tooth features, only for the aligning on arch form spline, which is free of penetration, the shell representation of the teeth themselves are used, in order to calculate the distances between them. By this it became possible to quantify clinically relevant figures in a natural manner and to almost entirely unlink the single operations of the process easily.

That means however, that little penetrations between the teeth of the mandible and the maxilla can occur in the created pre-set-up. Furthermore you can aim for solutions in the special planning of the treatment, which cannot be realised by the idealised process. An example would be the often used polishing of the front teeth.

Because of these and other reasons it may be necessary to make small manual corrections of the positions of the teeth after the automatic creation of the pre-set-up. These corrections can be made directly by the used system.

For the support of the user during these works, it is imaginable to join another automatic process, by which the penetration of the teeth is annulled. Such a process wouldn't be a direct part of the planning of the treatment, but it would only correct the possibly created physical contradictions, which are impossible practically.

For the realisation of such a process many proceedings can be used. An easy solution would be to move the teeth of the upper jaw e.g. into in vertical direction, until the penetrations are gone. However like this it can happen easily that the teeth have to be moved too far to e.g. correct a penetration, which has actually been created by e.g. the teeth sliding into each other vestibularly.

For this reason, a proceeding should be used, for which the teeth are not moved into an indicated direction in order to correct the penetrations of the teeth. Instead, the teeth of one or possibly both jaws keep all liberties compatible with the other teeth. That means the freedom of movement in vestibular/lingual an in occlusal/gingival direction.

It would now be the task of the procedure to move the considered tooth so that the liberty of penetration with the other teeth is achieved on one side, but also so that the movement, which removes the tooth from its original position (here given by the pre-set-up), is minimized.

Demonstration of a Surgery Case

Earlier, the working of the procedure described here was explained by way of examples.

Now, it will be shown how dysgnathism can be treated by the procedure demonstrated. This will be shown on a special case and it will be demonstrated in what way operative interventions can be regarded during the creation of the set-up.

Figure 34:
FIG. 34 shows the malocclusion of the dentition as if viewed from right. One can see the incomplete molar class relation as well as the front teeth, which are strongly inclined in the lingual direction. A back bite is shown. The view in FIG. 34 shows the back bite of the upper front teeth, the lingual tipped lower front teeth, and the incomplete molar class relation of the right molars.
Figure 35:
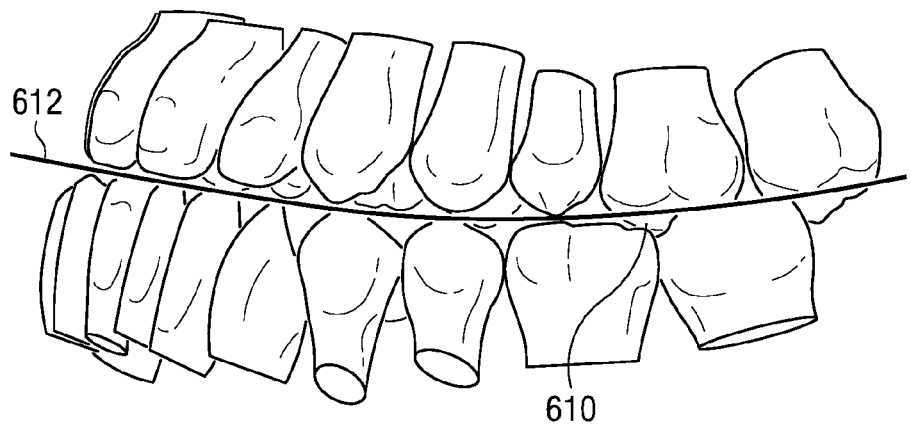
FIG. 35 shows the malocclusion dentition as if viewed from left. One can also see here the incomplete molar class relation of the left molars, as well as the distinction of a curve of spee.

The case given, FIGS. 34 and 35, shows an evident mandibular prognathism. That means the mandible comes to rest too far to anterior referring to the maxilla. Therefore it is a class I jaw relation. (The exact clinical indication doesn't matter here, since only the proceeding is to be demonstrated.)

The surgical operation will probably be, to shorten the jawbone on the left and right tail of the jawbones. Three tasks for the system described here result from this. The first is to evaluate the necessary posterior shortening of the mandible, the second is to prepare the patient for the operation, which happens here through a pre-surgery set-up, and the third task is to accomplish the final set-up under consideration of the position of the alveolar bone of the mandible in relation with the maxilla, which has been changed by the operation.

FIGS. 34 and 35 show the original situation of the patient, the malocclusion. You can see easily the lingual tipping of the front teeth of the mandible and the given back bite. The molars don't show an evident class relation, you can see however that a class I relation can be realised by the posterior displacement of the mandible aimed for. This goes for both sides of the set of teeth.

Furthermore one can see that this patient has a distinct curve of spee on the mandible, which shall be corrected.

From the labial point of view (FIG. 38) you can also see the slight cross bite of the lateral teeth, which shall be corrected as well.

FIG. 34 shows the malocclusion of the dentition in the view from right. One can see the incomplete molar class relation as well as the front teeth, which are strongly inclined to lingual. A (back bite) is given. The view in FIG. 34 shows the backbite of the upper front teeth 600, the lingual tipped lower front teeth 602, and the incomplete molar class relation of the right molars 604.

FIG. 35 shows the malocclusion des dentition in the view from left. One can also see here the incomplete molar class relation of the left molars 610, as well as the distinction of a curve of spee 612.

Figure 36:
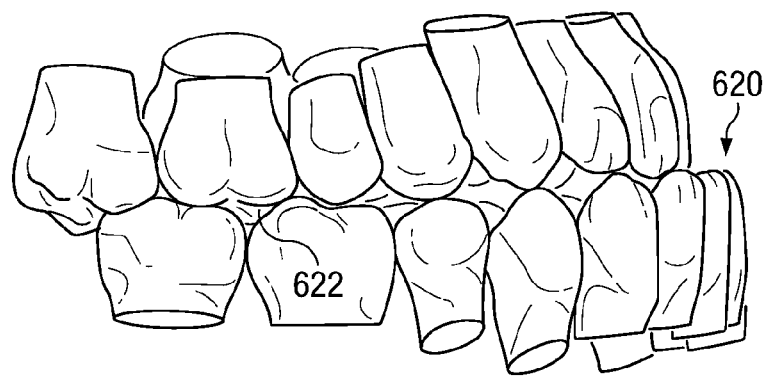
FIG. 36 shows the pre-surgery set-up for the maxilla and the mandible. The gap between UR7 and UR6 has been closed. The molars generally kept the position of the malocclusion. The crowding in the front has been removed. This leads firstly to an extreme back bite. The molar incomplete class relation is maintained.
Figure 37:
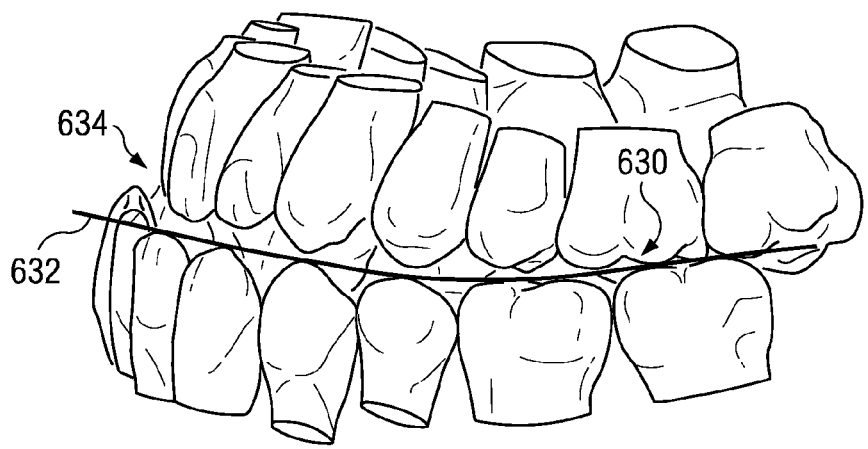
FIG. 37 shows the pre-surgery set-up from the left. One can see from this perspective, that the given curve of spee of the mandible has not been adjusted. That means the alignment on the surface plain has not been accomplished after the choice the user has made. The crowding of the teeth in the frontal area of the mandible has been removed. The molar incomplete class relation is maintained. An extreme back bite occurred at this stage.
Figure 38:
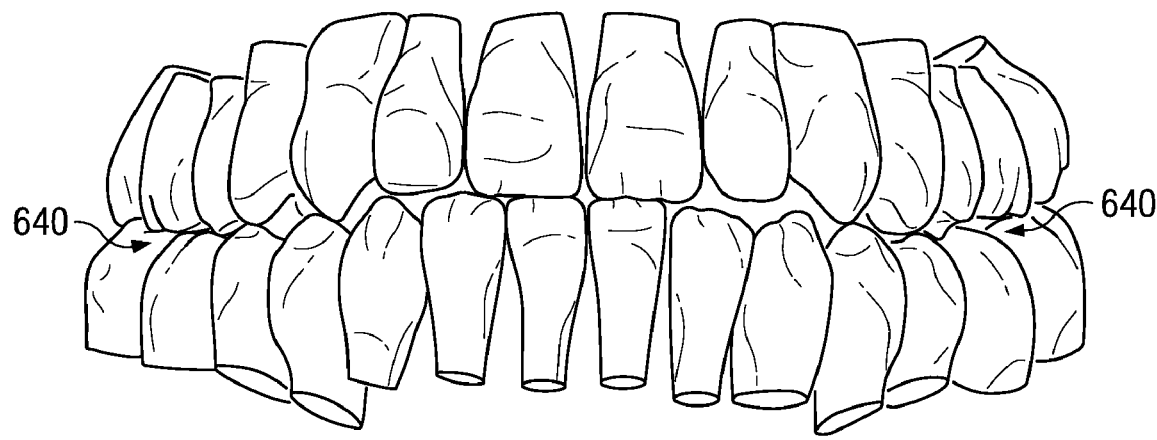
FIG. 38 shows the pre-surgery set-up from the labial view. One can see that the lateral cross bite remains, which can be remedied perhaps through surgery. Furthermore the teeth are aligned on the arch form spline, which means the vestibular/lingual correction and the necessary rotations have been accomplished.

In FIGS. 36, 37 and 38 the result of an automatically created presurgery set-up is demonstrated. For this, the jaws have been treated independently from each other. In this first step the align on occlusal surface has not been used for both jaws. That means that especially the curve of spee of the mandible has not yet been corrected. Furthermore the molar class relation has not been corrected, that means the molars reside in the same sagittal position referring to the malocclusion. The arch form has been built up symmetrically to the median plain.

One can see in FIG. 36, in comparison to FIG. 34, that the given crowding could be removed by the reduction of the tippings in the frontal area. The teeth are aligned horizontally and have been aligned on the arch form spline.

These operations have been accomplished automatically on the basis of the default parameterizing. Consequently the width and the shape in both jaws stayed almost unmodified referring to the malocclusion.

The flairing in the frontal area has been done by operation 10 of the sequential process presented earlier. For this, only a little manual displacement of the facial midline in the maxilla and in the mandible by 0.3 mm to the right was necessary.

FIG. 36 shows the pre-surgery set-up for the maxilla and the mandible from right. The gap between UR7 and UR6 has been closed. The molars generally kept the position of the malocclusion. The crowding in the front 620 has been removed. This leads firstly to an extreme back bite. The molar incomplete class relation 622 is maintained.

FIG. 37 shows the pre-surgery set-up from the left. One can see from this perspective, that the given curve of spee of the mandible 632 has not been adjusted. That means the alignment on the surface plain has not been accomplished after the choice the user has made. The crowding of the teeth in the frontal area of the mandible has been removed. The molar incomplete class relation 630 is maintained. An extreme back bite 634 occurred at this stage.

FIG. 38 shows the pre-surgery set-up from the labial view. One can see that the lateral cross bite 640 remains, which can be remedied perhaps through surgery. Furthermore the teeth are aligned on the arch form spline, which means the vestibular/lingual correction and the necessary rotations have been accomplished.

The surgery set-up created as described above fulfils two tasks at this point. First, it is possible to perform the surgery set-up directly on the patient, if this corresponds to the clinical indications.

Secondly, the surgery set-up can be used to simulate the bite which will result from the surgical operation.

Figure 39:
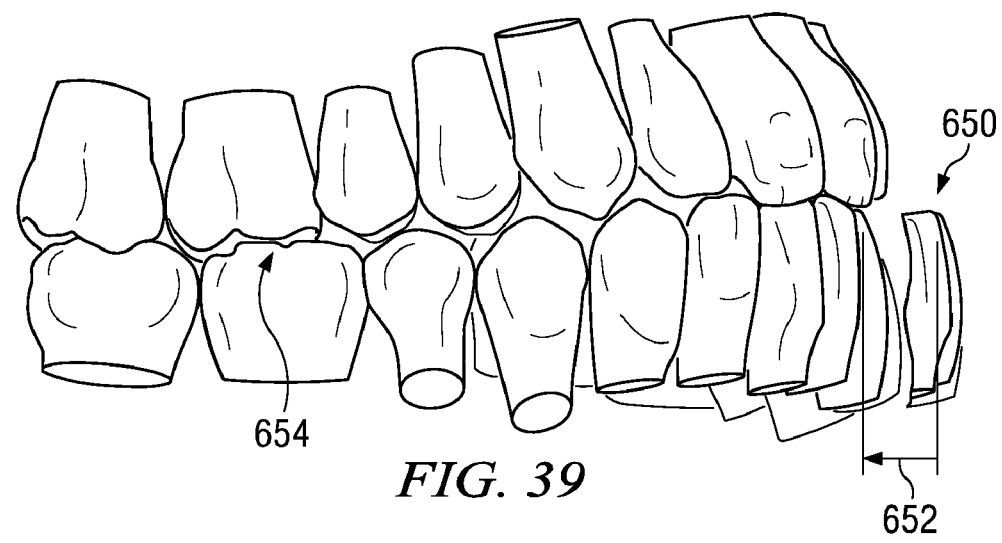
FIG. 39 shows AP-positions of the mandibular front of the surgery set-up, resulting lingual shift of the mandible by the surgery simulation, and adjustment of the correct molar class I relation.
Figure 40:
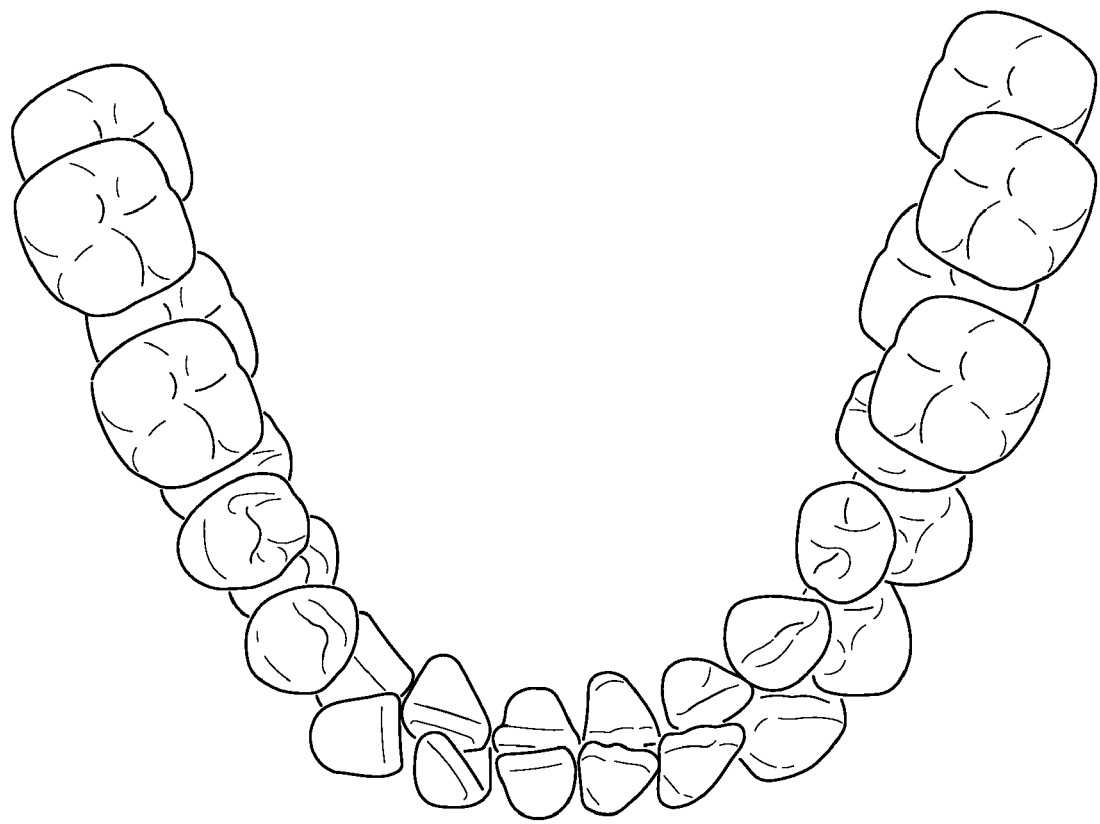
FIG. 40 shows again the simulation of the surgery interventions of the mandible from the occlusal view for a better visualisation. It is shown with the overlapping with the mandible in the position before the intervention. One can see clearly the complete displacement of the lower jaw into lingual direction.

This is demonstrated in FIGS. 39 and 40. In FIG. 39 you can see the view of the bite from the right after the simulated surgical shortening of the mandible. You can see, that the molar class I has been realised and that the shortening of the mandible lead to a acceptable maxilla-mandible relation in the front.

We want to press the point that the demonstrated steps of the planned treatment are only an example and are not necessarily the correct way of clinical proceeding for the given case. It is possible to motivate the surgery intervention differently than it has been demonstrated here, e.g. for the correction of the facial profile of the patient or after any other clinical indications.

Furthermore it is imaginable, to accomplish the simulation of the surgery intervention on the monitor before the demonstration of a corresponding x-ray image. With the correct scaling of the x-ray image and the 3D jaw model you can e.g. deduct directly the effect of the surgery intervention on the facial profile.

FIG. 39 shows the global posterior shift to solve the mandible pragmatism. FIG. 39 shows the resulting upper and lower jaw relation after shifting of the mandibular alveolar bone lingual. The desired molar class I relation is adjusted. Specifically, FIG. 39 shows AP-positions of the mandibular front of the surgery set-up 650, resulting lingual shift of the mandible by the surgery simulation 652, and adjustment of the correct molar class I relation 654.

FIG. 40 shows again the simulation of the surgery interventions of the mandible from the occlusal view for a better visualisation. It is shown with the overlapping with the mandible in the position before the intervention. One can see clearly the complete displacement of the lower jaw into lingual direction.

The simulation of the surgery intervention accomplished like this is also important for the position of the alveolar reference spline, since it is moved by the same amount as the mandible during this action. By this it is guaranteed that the virtual root center still have the same relation with the virtual parodont after the intervention. That means the physical movement of the alveolar bone is followed numerically in this manner.

Figure 41:
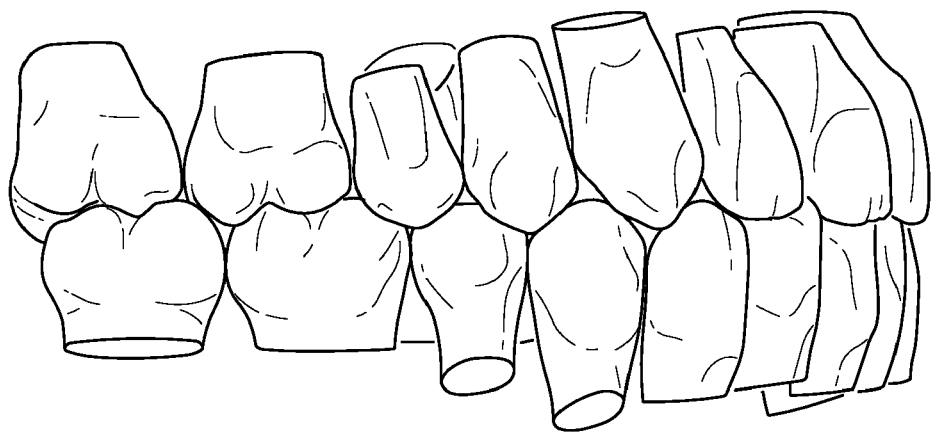
FIG. 41 shows the automatic pre-set-up in the view from right.

FIG. 41 shows the automatic pre-set-up in the view from right.

Figure 42:
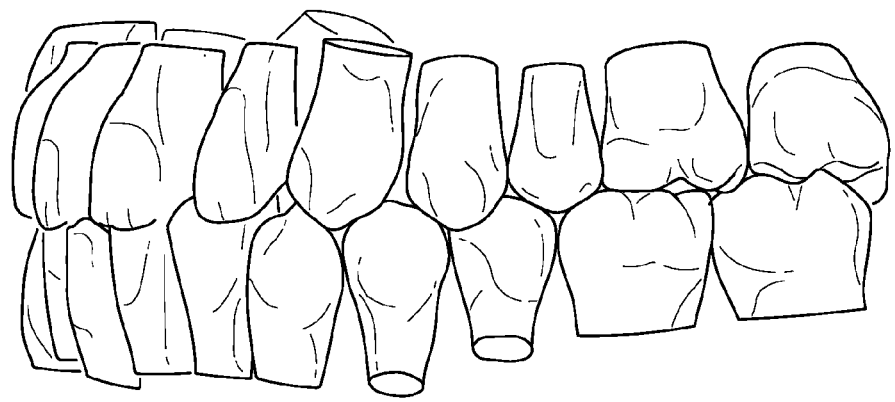
FIG. 42 shows the automatic pre-set-up in the view from left.

FIG. 42 shows the automatic pre-set-up in the view from left.

Figure 43:
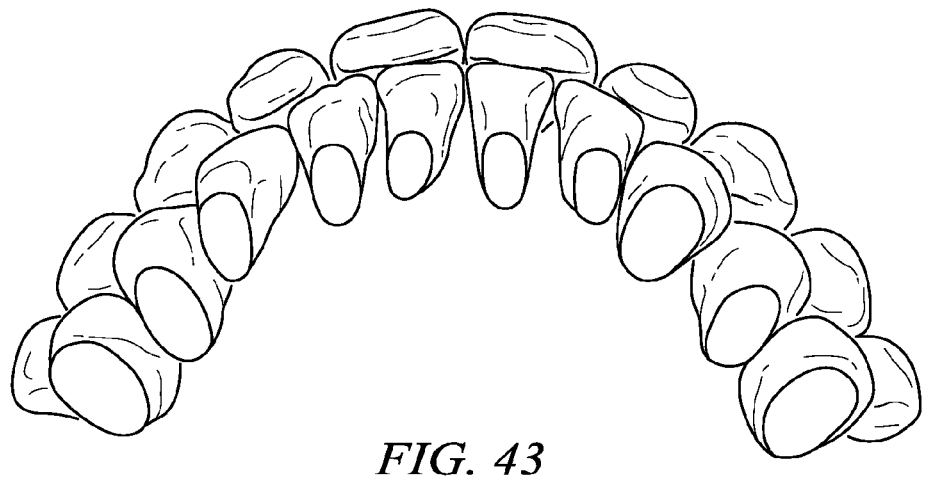
FIG. 43 shows the front part of the pre-set-up with the resulting gaps of maxilla.

FIG. 43 shows the front part of the pre-set-up with the resulting gaps of maxilla.

Figure 44:
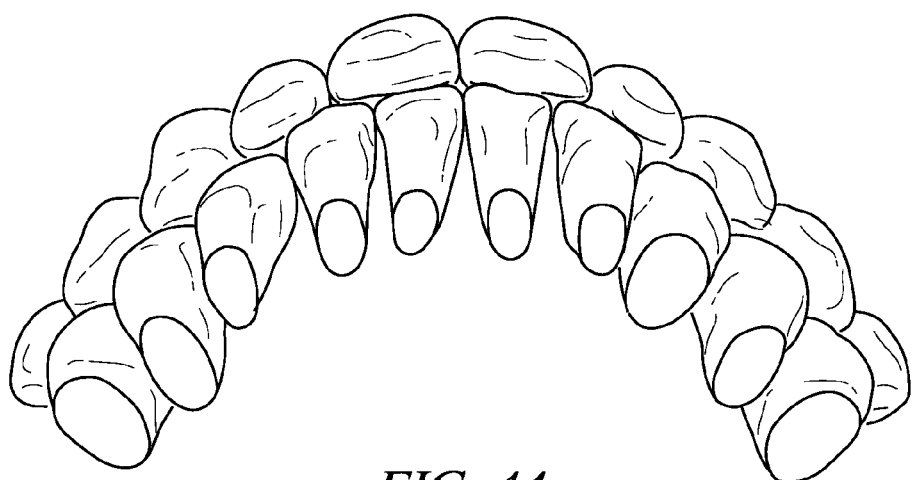
FIG. 44 shows the front part of the final set-up after reducing the canine distance.

FIG. 44 shows the front part of the final set-up after reducing the canine distance.

According to another aspect of the invention, a global reference system is disclosed.

Yet in another aspect of the invention, a system, comprising a computing device, memory, and a set of software instructions is provided for quickly arriving at a virtual pre-set-up of the orthodontic treatment plan for a patient, based up on the user specified parameters; and thereafter enabling the user interactively arrive at a final, desired treatment set-up for the patient. The parameter types and values utilized in the treatment planning process are common to the orthodontic discipline. Moreover, in one aspect of the invention, a default parameter set is provided that the user can optionally choose for obtaining the pre-set-up automatically. The software instructions provided for creating the pre-set-up relies heavily on a set of parameters describing the jaw characteristics as well as the jaw interrelations. The tooth-root movements are confined to a necessary minimum as the pre-set-up meets various criteria towards an optimum. The pre-set-up software instructions perform automatically all global tasks such as guidance of the tooth roots, adjustment of the intercuspidation of the molars, space management in the frontal area and creation of an occlusion to an optimum. The underlying mathematical model and rules consider typical details like frontal overjet, overbite and molar classes. It supports the space management for virtual or real tooth extractions. Space can also be reserved for later implantations. The software instructions allow selection of global arch form to account for specific characteristics of a single jaw. Arch forms from the database library may be used (e.g. straight wire technique). Additionally, a method is provided for the user to derive the arch form manually, e.g., from the malocclusion. The method also enables the user in devising an oral surgery, when applicable and desired, such as maxillary or mandibular prognathism/retrognathism. The treatment planning process is divided into sub-operations that simulate the work-flow of an orthodontist or dental technician. The occlusion is formed independently from the global form of the jaw and vice versa; or the consequences from parameter changes like the AP position of the anterior teeth are be displayed instantaneously without modifying other constraints, such as the frontal overjet. The operations enabled by the software instructions can be summarized as follows:

1. obtain (a) a three-dimensional virtual model of a patient in malocclusion or any mid-treatment stage, and (b) tooth-features; and deriving there from;
2. derive (a) a global reference system, (b) Curve of Wilson (optional), molar torque, and (c) relations of upper and lower jaw;
3. sub-operations to generate the orthodontic pre-set-up
    (a) find the Alveolar Reference Curve;
    (b) determine the filter of controlled tipping of tooth-root including parameterization of the controlled tipping filter;
    (c) find the occlusal surface;
    (d) vertically align the occlusal surface; (i) parameterize the occlusal surface; and (ii) parameterize the alignment operation on the occlusal surface;
    (e) find the arch form;
    (f) align teeth on the arch form spline;
    (f) parameterize the shape of the arch form spline: (i) derive of the arch form splines from a reference jaw; and (ii) derive the breadth of the jaw; and
    (g) parameterize the aligning on arch form: (i) AP-Position of the molars; (ii) interproximal distances; (iii) standardization of the frontal overjet; (iv) standardization of the molar relation (Angels classes); and (v) midline for the jaw specifically correction of the global facial midline.

Presently preferred and alternative embodiments of the invention have been set forth. Variation from the preferred and alternative embodiments may be made without departure from the scope and spirit of this invention.

We claim:

1. A system for quickly arriving at a virtual pre-set-up of the orthodontic treatment plan for a single jaw of interest, either lower or upper, of a patient, comprising:
    A. a computing device; and
    B. a memory unit operably connected to said computing device; wherein said memory stores virtual 3D dentition model of a patient, a reference coordinate system, and the user specified parameters; and wherein said memory stores treatment planning instructions for performing the tasks comprising:
    a. obtaining a three-dimensional virtual model of the dentition of a patient; wherein said virtual model of the dentition comprises the upper jaw and upper teeth, the lower jaw and lower teeth, and virtual tooth roots for said upper teeth and said lower teeth;
    b. obtaining tooth-features derived from said upper teeth and said lower teeth; wherein said tooth-features comprise cusp tips, incisal edges, marginal ridges, central groove lines, buccal grooves, contact points;
    c. determining upper occlusal surface corresponding to said upper jaw;
    d. determining lower occlusal surface corresponding to said lower jaw;
    e. determining a horizontal plane from said upper occlusal surface and said lower occlusal surface; wherein said horizontal plane is calculated as a balance between said upper occlusal surface and said lower occlusal surface;
    f. identifying, as the case may be, either said upper jaw or said lower jaw as the single jaw of interest;
    g. defining a reference co-ordinate system; wherein said reference co-ordinate system comprises x, y and z axes; wherein said x-axis is the sagittal axis, said y-axis is the transversal axis, and said z-axis is the vertical axis;
    h. determining virtual tooth root resistance centers for said virtual tooth roots of the teeth of said single jaw of interest;
    i. finding an Alveolar Reference Curve using the sub-steps comprising:
        (1) projecting said virtual tooth root resistance centers onto said horizontal plane, thereby producing the projected centers;
        (2) fitting a planar convex curve to said projected centers whereby the sum of squares of the two-dimensional distances between the projected centers and the convex curve is minimized while maintaining the convexity of the convex curve; and
        (3) labeling the convex curve the Alveolar Reference Curve;
    j. determining controlled tipping filter from said Alveolar Reference Curve; wherein said controlled tipping filter is a record of said two-dimensional distances between said projected centers and said Alveolar Reference Curve;
    k. creating the arch form spline for said single jaw of interest by connecting with a smooth planar curve projections of buccal cusp tips of molar teeth and lateral edges of anterior teeth into said occlusal plane of said single jaw of interest; and
    l. performing alignment of the teeth of said single jaw of interest while restricting the tooth movement along said x, y and z axes of said reference co-ordinate system; and controlling the virtual tooth-root center movement with said controlled tipping filter; wherein said alignment is done with respect to said occlusal surface and with respect to said arch form spline of said treatment pre-set-up jaw; using the sub-steps comprising:
        (1). determining relative transversal position of the incisal contact points using the standardized offset value;
        (2). aligning on arch form spline using standardized fixed interproximal distances;
        (3). aligning on the occlusal surface using standardized offset values for the vertical position of the teeth;

(4). performing mesiodistal shift of the lateral segments for the standardization of the desired molar class; and (5). adjusting possibly created interproximal gaps or intersections in the front by the equal distribution of all created gaps or intersections on the individual interproximal distances on the left and the right half of the jaw.

2. The system of claim 1, wherein said three-dimensional virtual model of the dentition of a patient is in a malocclusion stage.

3. The system of claim 1, wherein said three-dimensional virtual model of the dentition of a patient is in a mid-treatment stage.

4. The system of claim 1, wherein said upper occlusal surface minimizes the sum of squares of the vertical distances between said upper occlusal surface and the marginal ridges of the molars, and said upper occlusal surface and the incisal edges of the centrals.

5. The system of claim 1, wherein said lower occlusal surface minimizes the sum of squares of the vertical distances between said lower occlusal surface and the cusp tips, and said lower occlusal surface and the lateral edges of the anteriors.

6. The system of claim 1, wherein said virtual tooth root resistance centers are approximated from the length of the transition line between the dentine and the jaw bone determined from said virtual model of the dentition.

7. The system of claim 1, further comprising the instructions for:

A. aligning again on said arch form spline in order to correct interferences with the vertical alignment.

8. The system of claim 1, wherein said reference co-ordinate system is a global reference system; where in said global reference system is derived from said virtual model of the dentition and said horizontal plane; wherein said global reference system comprises x, y and z axes; wherein said x-axis is the sagittal axis, said y-axis is the transversal axis, and said z-axis is the vertical axis; wherein said x axis and said y axis are contained in said horizontal plane; wherein said x axis and said z axis are contained in a median plane; wherein said median plane runs through the incisive contact point of central teeth of said single jaw of interest, and wherein said median plane is located equal distances from molar teeth to the sagittal axis form right half of said single jaw of interest and left half of said single jaw of interest.

9. The system of claim 8, wherein said reference co-ordinate system is obtained by adjusting said global reference system.

* * * * *